United States Patent
Strelchenok et al.

(10) Patent No.: US 6,642,271 B2
(45) Date of Patent: Nov. 4, 2003

(54) POTENTIATING COMPOUNDS

(75) Inventors: Oleg Strelchenok, Lidingö (SE); Julian Aleksov, Lidingö (SE)

(73) Assignee: Ardenia Investments, Ltd., London (GB)

( * ) Notice: Subject to any disclaimer, the term of this patent is extended or adjusted under 35 U.S.C. 154(b) by 0 days.

(21) Appl. No.: 10/098,873

(22) Filed: Mar. 15, 2002

(65) Prior Publication Data

US 2003/0050343 A1 Mar. 13, 2003

Related U.S. Application Data

(60) Provisional application No. 60/302,790, filed on Jul. 3, 2001.

(30) Foreign Application Priority Data

May 15, 2001 (SE) .............................................. 0101702

(51) Int. Cl.[7] ........................ A01N 37/12; A01N 37/44; A61K 31/195; C07D 493/00; C07C 313/00
(52) U.S. Cl. ...................... 514/562; 514/563; 514/710; 549/510; 562/58; 562/126
(58) Field of Search ................... 562/58, 126; 514/562, 514/563, 710

(56) References Cited

U.S. PATENT DOCUMENTS

| | | | |
|---|---|---|---|
| 4,459,404 A | 7/1984 | Frieckel et al. | 548/253 |
| 4,618,685 A | 10/1986 | McCully | 549/63 |
| 5,827,533 A | 10/1998 | Needham | 424/450 |
| 5,968,940 A | 10/1999 | Han et al. | 514/261 |
| 6,040,342 A | 3/2000 | Rephaeli et al. | 514/548 |
| 6,043,277 A | 3/2000 | Rephaeli et al. | 514/548 |
| 6,054,595 A * | 4/2000 | Kazimir et al. | 549/63 |
| 6,274,742 B1 | 8/2001 | Kazimir et al. | 549/63 |

FOREIGN PATENT DOCUMENTS

| | | |
|---|---|---|
| DE | 40 32 187 | 4/1992 |
| DE | 40 32 187 A1 | 4/1992 |
| EP | 0 280 741 | 9/1988 |
| WO | WO 96/40055 | 12/1996 |
| WO | WO 98/00127 | 1/1998 |
| WO | WO 00/61537 | 10/2000 |
| WO | WO 00/61541 | 10/2000 |
| WO | WO 01/12584 | 2/2001 |
| WO | WO 01/93836 | 12/2001 |

OTHER PUBLICATIONS

Goodman & Gilman's The Pharmacological Basis of Therapeutics, 10th ed., pp. 1381–1388. McGraw–Hill (2001).*

Vaughan, J.R., Jr. "Acylalkylcarbonates as Acylating Agents for the Synthesis of Peptides" JACS, vol. 73, p. 3547 (1951).*

Faith, Keyes, and Clark's Industrial Chemicals, Fourth Edition, "Sodium Carbonate," pp. 706–715 John Wiley & Sons (1975).*

Kalemkerian et al., Activity of fenretinide plus chemotherapeutic agents in small–cell lung cancer cell lines, Cancer Chemother Pharmacol, (1999) 43:145–150.

Kim et al., In vivo evaluation of polymeric miceller paclitaxel formulation: toxicity and efficacy, Journal of Controlled release, 72(2001) 191–202.

Zhang et al., An investigation of the antitumour activity and biodistribution of polymeric micellar paclitaxel, Cancer Chemother Pharmacol, (1997) 40:81–86.

Arsenov, D.V. et al. (2001) "Synthesis of N–(all–trans–retinoyl) doxorubicin and Study of the Antitumor Activity of its Complex with Blood Serum Proteins" *Pharmaceutical Chemistry Journal* 35 (4): 186–189 (Original and English translation).

* cited by examiner

Primary Examiner—Richard L. Raymond
Assistant Examiner—Zachary C. Tucker
(74) Attorney, Agent, or Firm—Morrison & Foerster LLP

(57) ABSTRACT

This invention relates to novel compounds, capable of potentiating the efficacy of therapeutically active compounds, for example cytotoxic compounds used in the treatment of cancer. The novel compounds have been shown to increase the pharmacological activity of a conventional paclitaxel formulation and to make it possible to manufacture a new formulation of paclitaxel, exhibiting improved solubility, improved storage properties, and increased therapeutic efficacy as shown in the enclosed examples.

36 Claims, No Drawings

POTENTIATING COMPOUNDS

RELATED APPLICATIONS

This application claims priority to Swedish Application No. SE 0101702-9 filed May 15, 2001 and United States Provisional Application No. 60/302,790 filed Jul. 3, 2001, each of which are hereby incorporated by reference.

FIELD OF THE INVENTION

This invention relates to novel compounds having therapeutic properties in themselves, and being capable of potentiating the efficacy of other therapeutically active compounds, for example cytotoxic compounds used in the treatment of cancer. The novel compounds have been shown to possess a cell growth inhibiting property, and in addition to this, also to increase the pharmacological activity of a conventional paclitaxel formulation and to make it possible to manufacture a new formulation of paclitaxel, exhibiting improved solubility and therapeutic efficacy.

BACKGROUND OF THE INVENTION

While the term "chemotherapy" originally had a very broad meaning, encompassing the treatment of various diseases with chemical agents, it has today a more specific meaning. In modern language, the term "chemotherapy" usually refers to the use of chemical agents to destroy cancer cells. Among the chemical agents currently used as anticancer drugs, most function by impairing the ability of the cancer cells to replicate by interfering with DNA and RNA activities associated with cell division.

Paclitaxel is a diterpenoid compound {(2R,3S)-3-Benzamido-3-fenyl-2-hydroxy propionic acid-[(2aR, 4S, 4aS, 6R, 9S, 11S, 12S, 12aR, 12bS)-6,12b-diacetoxy-12-benzoyloxy-2a, 3, 4, 4a, 5, 6, 9, 10, 11, 12, 12a, 12b-dodecahydro-4,11-dihydroxy-4a, 8, 13, 13-tetramethyl-7, 11-methano-5-oxo-1H-cyclodeca[3,4]benz[1,2-b]oxet-9-yl] ester, the active ingredient in Taxol®, Bristol-Myers Squibb} originally isolated from the western yew, a cone-bearing evergreen tree of the genus Taxus. Paclitaxel is one example of an important chemotherapeutic agent or anticancer drug currently in use. It has a wide spectrum of activity against solid tumours: primarily breast cancer, ovarian, colon and non-small cell lung carcinomas. It binds to the β-subunit of tubulin, resulting in the formation of stable non-functional microtubule bundles and thus interfering with mitosis. The drug can also induce apoptosis and has anti-angiogenic properties.

Paclitaxel is highly protein-bound, has large volumes of distribution, but poor penetration into the central nervous system. This compound is primarily eliminated from the body via hepatic metabolism, and its use is therefore generally precluded in severe hepatic dysfunction.

In recent years, considerable emphasis has been given to the development of new formulations of paclitaxel that are suitable for intravenous administration, in order to address the solubility and toxicity issues associated with this particular drug. Examples include dispersed systems such as emulsions, liposomes, mixed micelles prepared by co-precipitation using bile salts and phospholipids (Alkan-Onyuksel H, et al. Pharm. Res. vol 2. pp. 206–212, 1994), cyclodextrins, and microspheres. Water-soluble prodrugs such as polyethylene glycol- and polyglutamate-paclitaxel with promising antitumor activity have also been developed.

The commercially available product, Taxol® (a paclitaxel concentrate for preparation of solutions for infusion, marketed by Bristol-Myers Squibb Co., New York, N.Y., USA), is currently formulated in a vehicle containing a mixture of polyoxyethylated castor oil (Cremophor® EL) and ethanol, in the approximate proportions 1:1 (v/v). Cremophor® EL, which is a commonly used surfactant for lipophilic compounds, has however been associated with adverse side-effects, such as bronchospasms, hypotension, and other manifestations of hypersensitivity particularly following rapid administration. Therefor, long infusion times, high dilution of the ethanol:Cremophor® EL solution, and pre-medication (e.g. using corticosteroids, antihistamine, and H2-blockers) are actions resorted to in order to reduce these adverse effects.

Furthermore, the commercially available formulation is associated with a number of difficult technical issues such as stability, including the possibility of drug precipitation upon dilution, filtering requirements and restrictions regarding the use of PVC-containing vessels and administration sets. It is thus apparent that there is a need for a new formulation of paclitaxel that is efficacious and less toxic than the commercial product and which formulation can alleviate the side-effects and set aside the problems currently associated with preparation and administration of this drug.

Further, the small difference between the therapeutic and the toxic concentration severely limits the clinical usefulness of paclitaxel. The therapeutic efficacy could be improved by delivering the drug with an appropriate microcarrier system, which is able to change temporal and spatial biodistribution of the drug. This approach has been suggested for the highly toxic and poorly soluble amphotericin B, which has been successfully incorporated into disk-like micelles of cholersteryl sulphate (Lasic D. D. Nature. Vol. 355, 16 Jan., pp. 279–280, 1992).

In later years, great deal of effort has been given to the development of polymeric micellar paclitaxel formulations using amphiphilic diblock copolymers (K. Kataoka et al., JMS-Pure Appl. Chem. A31 (11), pp. 1759–1769, 1994).

In one study, using a human cancer cell line model, a new formulation containing biodegradable amphiphilic diblock copolymer, monomethoxy poly(ethylene glycol)-block-poly (D,L-lactide) (m PEG-PDLLA) and paclitaxel (Genexol®-PM) and Taxol® showed comparable in vitro cytotoxicity at the same concentrations. The polymeric micellar formulation of paclitaxel produced an increase in a maximum tolerated dose (MTD) as compared with that of Taxol® when administered i.p. in vivo. This formulation was said to have advantages over the commercially available injectable preparation of Taxol® in terms of low toxicity levels and increased paclitaxel dose (2 to 3-fold higher levels) (Kim S. C. et al., J. Controlled Release, v.72, pp. 191–202, 2001).

The advantages mentioned by the above authors are related to the slow release of paclitaxel from the micelles, due to a strong hydrophobic association between paclitaxel and the high molecular weight m PEG-PDLLA. At the same time, according to the authors, additional studies of a polymeric micellar formulation, comprising paclitaxel in unusually high doses will be required to fully characterize the nature of toxicities and especially the more distant consequences this kind of treatment.

The present inventors have taken a principally different approach. They have made available novel compounds, comprising the residues of naturally occurring substances only. These compounds, numbered I through VI, in themselves have low toxicity. A single dose i.p. toxicity study in rats was carried out in accordance with the OECD principles of Good Laboratory Practice. It was found that the compounds I–VI, at a dose level of 100 mg/kg body weight did not produce mortality. The minimal lethal dose is thus above 100 mg/kg body weight for these compounds (I–VI).

Considering "chemotherapy" in it widest meaning, i.e. the administration of chemical agents for the prevention, treatment or alleviation of a medical condition, a manifold of similar problems arise. It is important to optimise efficacy, e.g. the uptake and target-specificity of the compound, its distribution in the body and its clearance, simultaneously as minimising the possible side-effects, risks to medical staff etc. Also the cost of production, ease of preparation, modes of administration, stability during storage etc must be taken into consideration. In particular, it is desirable to be able to increase the solubility and bio-availability of poorly soluble pharmaceutical agents, increasing their efficacy and reducing their side-effects.

Considering "chemotherapy" in its more specific meaning, i.e. the use of chemical agents to destroy cancer cells, it remains an urgent task to make available new substances and formulations, which at least exhibit improved efficacy and less side-effects, but preferably also improved characteristics concerning solubility, safety, stability etc.

In particular, it is desirable to make available a new formulation of paclitaxel, exhibiting improved stability, improved efficacy and reduced side-effects, compared to presently available formulations. Further problems and the corresponding innovative solutions will be evident from the following description and claims.

Prior Art

DE 40 32 187 (Hermes Fabrik pharmazeutischer Präparate Franz Gradinger GmbH & Co., DE) discloses various N-Retinoyl-L-aminomercapto compounds and their physiologically acceptable salts. The compounds are suggested for use in the systemic and topical treatment of diseases of the mucous membranes. A closer study of the structural formulas reveals that structural elements, central for the compounds (I–VI) according to the present invention are absent or different in DE 40 32 187. Notably, the compounds of DE 40 32 187 contain a sulphur in oxidation state –2 and –1 respectively. The physiological function, as well as the physical and chemical properties of these sulphur containing compounds are determined by this oxidation state. There is also no indication that these compounds would influence the properties of paclitaxel or other water-insoluble or sparingly soluble substances.

Kalemkerian et al., Activity of fenretinide plus chemotherapeutic agents in small-cell lung cancer cell lines, *Cancer Chemother Pharmacol,* (1999) 43:145–150. This article describes a synthetic retinoid which is both a potent inducer of apoptosis in cancer cells, and which may have the capability of enhancing the activity of other cytotoxic agents. All combination studies were performed with a range of concentrations of each individual agent and both agents together at a fixed ratio corresponding to the ratio of the $IC_{50}$ values of each agent alone as identified in preliminary experiments. The authors state that their study does not make it possible to say whether the experimental agents interacted in a mutually exclusive or mutually nonexclusive manner. The issues of solubilisation and storage of paclitaxel or other water-insoluble or sparingly soluble pharmaceuticals is not discussed.

Zhang et al., An investigation of the antitumour activity and biodistribution of polymeric micellar paclitaxel, *Cancer Chemother Pharmacol,* (1997) 40:81–86. In this study, the conventional Cremophor Paclitaxel formulation was compared to a polymeric micellar paclitaxel, administered by i.p. injection. A biodegradable amphiphilic diblock copolymer, monomethoxy poly (ethylene glycol) block-poly (D,L-lactide) [mPEG-PDLLA] was used. The micellar formulation showed very promising results. The advantages mentioned are however related to the slow release of paclitaxel from the micelles, due to strong hydrophobic association between paclitaxel and the high molecular weight mPEG-PDLLA. Further, the toxicity and the long-term consequences of this slow release mode of administration need to be further studied.

Short Summary of the Invention

The present inventors have found that therapeutically active compounds can be dissolved in micelles of a compound which itself displays the desired therapeutic activity or an activity favourably interacting with or potentiating the desired activity, and which compounds exhibit low toxicity. The present invention thus makes available a group of new compounds, N-(all-trans-Retinoyl)-L-cysteic acid (I), N-(13-cis-Retinoyl)-L-cysteic acid (II), N-(all-trans-Retinoyl)-L-homocysteic acid (III), N-(13-cis-Retinoyl).L-homocysteic acid (IV), N-(all-trans-Retinoyl)-L-cysteinesulfinic acid (V), and N-(13-cis-Retinoyl)-L-cysteinesulfinic acid (VI), which exhibit therapeutic effects per se, and which in combination with known pharmaceuticals exhibit a synergistic effect. In combination with cytotoxic or cytostatic pharmaceuticals, said novel compounds introduce improved possibilities to combat cancer. Further, the present invention discloses a possibility of making water-soluble formulations of water-insoluble or sparsely soluble pharmaceuticals, such as paclitaxel, with enhanced pharmacological activity and improved storage and handling properties.

Description of the Invention

The terms "potentiation" and "potentiating" are used to define an action by which the therapeutic effect of two or more compounds, given simultaneously or substantially simultaneously, is greater than the effect of said compounds given separately.

The term "simultaneously" should in this context be interpreted broadly, i.e. encompassing both situations where two or more compounds are given in admixture, and situations where the compounds are administered separately, either via the same or different routes of administration, at the same time or sequentially, provided that the compounds exert their therapeutic influence in the body at the same or practically the same time.

The term "critical micell concentration" or "CMC" is a measure of the concentration of a solution component, which represents a critical value above which increasing concentration of said component forces the formation of micelles.

The present inventors have surprisingly found that N-(all-trans-Retinoyl)-L-cysteic acid (I),N-(13-cis-Retinoyl)-L-cysteic acid (II), N-(all-trans-Retinoyl)-L-homocysteic acid (III), N-(13-cis-Retinoyl)-L-homocysteic acid (IV), N-(all-trans-Retinoyl)-L-cysteinesulfinic acid (V), and N-(13-cis-Retinoyl)-L-cysteinesulfinic acid (VI) are capable of increasing the solubility of sparsely soluble compounds, as well as potentiating their therapeutic efficacy.

These novel compounds according to the present invention are amides of all-trans-retinoic acid or 13-cis-retinoic acid with L-cysteic acid (3-sulfo-L-alanine), L-homocysteic acid, L-cysteinesulfinic acid. The structural formulas of these compounds are presented below:

(I)
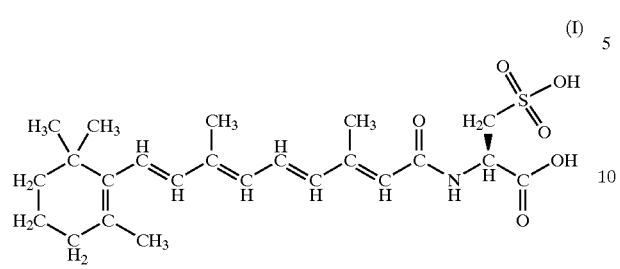
N-(all-trans-Retinoyl)-L-cysteic acid (II)
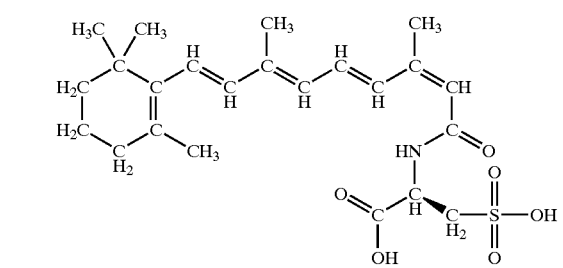
N-(13-cis-Retinoyl)-L-cysteic acid (III)
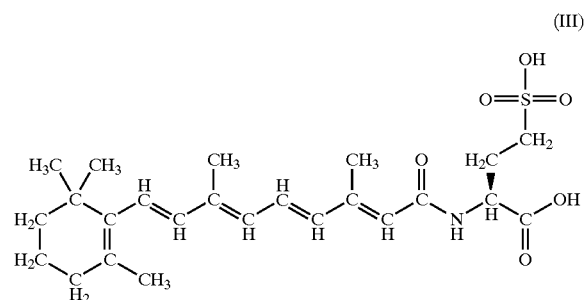
N-(all-trans-Retinoyl)-L-homocysteic acid (IV)
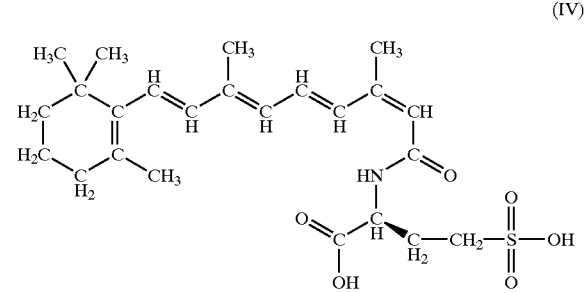
N-(13-cis-Retinoyl)-L-homocysteic acid (V)
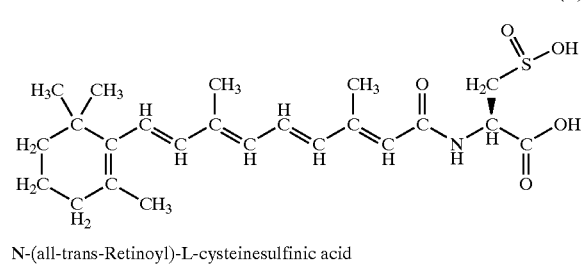
N-(all-trans-Retinoyl)-L-cysteinesulfinic acid -continued (VI)
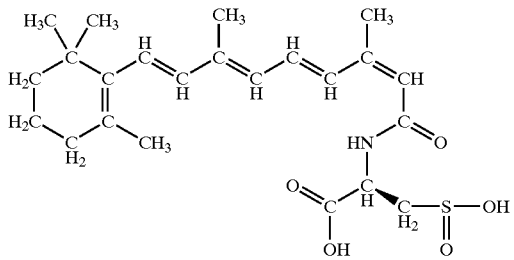
N-(13-cis-Retinoyl)-L-cysteinesulfinic acid The molecules of these compounds simultaneously exhibit a hydrophilic and a hydrophobic part in water solutions. In the form of salts, these compounds are capable of forming micelles in aqueous solutions at concentrations equal to or higher than the critical micelle concentration (CMC).

The present invention makes available the use of the above compounds, or derivatives thereof, for the manufacture of a medicament. The present invention also makes available the use of the above compounds, or a derivative thereof, for the manufacture of a medicament for the treatment of cancer.

Further, the present invention makes available a pharmaceutical composition comprising an active substance in a therapeutically effective amount, and one of the above compounds (compounds I–VI), or a derivative thereof. In particular, the present invention makes available a pharmaceutical composition wherein the active substance is a cytotoxic compound, and the potentiating compound is one of the above compounds (compounds I–VI), or a derivative thereof. According to one embodiment of the invention, said active substance is paclitaxel.

Another embodiment of the present invention is a method for potentiating the efficacy of a pharmaceutically active substance, wherein said substance is prepared in micellar form with at least one of the above compounds (compounds I–VI), or a derivative thereof.

Another embodiment is a method for increasing the solubility of a pharmaceutically active substance, wherein said substance is prepared in micellar form with at least one of the above compounds (compounds I–VI), or a derivative thereof.

Yet another embodiment is a method for improving the bio-availability of a pharmaceutically active substance, wherein said substance is prepared in micellar form with at least one of the above compounds (compounds I–VI), or a derivative thereof.

The present invention also makes available a method for the treatment of cancer, wherein a cytotoxic substance is mixed with at least one of the compounds above (compounds I–VI), or a derivative thereof, and delivered to a patient. In particular, the invention concerns such a method, wherein the cytotoxic substance is paclitaxel.

The inventors have shown that the poorly soluble compound paclitaxel can be dissolved in micelles of N-(all-trans-Retinoyl)-L-cysteic acid (I), N-(13-cis-Retinoyl)-L-cysteic acid (II), N-(all-trans-Retinoyl)-L-homocysteic acid (III), N-(13-cis-Retinoyl)-L-homocysteic acid (IV), N-(all-trans-Retinoyl)-L-cysteinesulfinic acid (V), and N-(13-cis-Retinoyl)-L-cysteinesulfinic acid (VI), creating mixed micelles. In this way, an excellent solubility of paclitaxel in the form of mixed micelles in saline was achieved. Solutions of these compounds (compounds I–VI) in saline were prepared in a wide range of concentrations, and added in MEM with 5% fetal bovine serum (FBS) to cultures of human breast adenocarcinoma (the MDA-MB-231 cell line).

Tests evaluating the cytotoxicity of the inventive compounds in the concentration 40 nM have shown that better results are obtained in the range 0,005 mg/ml to 5,0 mg/ml of the compounds in saline (initial concentrations). A maximum cell growth inhibition close to 38% was observed at the initial concentration 1 mg/ml (in saline) before addition to the adenocarcinoma cultures (the MDA-MB-231 cell line).

Tests evaluating the cytotoxicity of the inventive compounds in the concentration range $10^{-11}$ M to $10^6$ M in cultures of MDA-MB-231 cells have revealed the following dependence: An increase of the concentrations of the inventive compounds led to the enhancement of cell growth inhibition, achieving a value close to 42% at the concentration $10^{-6}$ M.

The cytotoxicity of the formulation of paclitaxel/compound (I–VI), and compounds I through VI alone, was compared with paclitaxel and Taxol® in cultures of MDA-MB-231 cell line. In the case of paclitaxel and Taxol®, the cell growth inhibition approached 46% at concentrations close to the $IC_{50}$ concentration.

In particular at the same paclitaxel concentration, the formulation of paclitaxel and compound I or paclitaxel and compound II, both at a molar ratio of the components of 1:5, exhibited a surprisingly high cell growth inhibition of 70%. The extent of cell growth inhibition using the commercially available Taxol® (positive control) was 45%. Already the cytotoxic action of compounds I or II alone, at a concentration of 40 nM, was close to 40%. The formulations of paclitaxel and compound I (or compound II) display an increasing cell growth inhibition within the molar ratio range 1:3–1:5 (paclitaxel:compound I (or compound II)). When further increasing the ratio of the components to 1:10, the extent of the cell growth inhibition remains practically unchanged.

The inventive formulation of N-(all-trans-Retinoyl)-L-cysteic acid (I), N-(13-cis-Retinoyl)-L-cysteic acid (II), N-(all-trans-Retinoyl)-L-homocysteic acid (III), N-(13-cis-Retinoyl)-L-homocysteic acid (IV), N-(all-trans-Retinoyl)-L-cysteinesulfinic acid (V), N-(13-cis-Retinoyl)-L-cysteinesulfinic acid (VI) and paclitaxel is prepared as follows: Solutions of paclitaxel and any compound (I–VI) in ethanol (or other aliphatic alcohol) are first prepared in appropriate concentrations. Then aliquots of these solutions are mixed to form a mixed solution with the desired molar ratio paclitaxel:compound (I–VI). The obtained solution can be stored for at least three months at low temperatures, without noticeable change in the properties of compound (I–VI). Moreover, the formulation retains its cytotoxic effects during prolonged storage. Before use, the solution is evaporated in vacuo to yield a waxy solid which is dissolved in saline or other commonly used vehicle for intravenous infusion to a patient. Taxol® (Bristol-Myers Squibb Co.) is a formulation containing Paclitaxel (6 mg), ethanol (396 mg) and Cremophor® EL (527 mg). The present inventors have shown that the inventive compounds, N-(all-trans-Retinoyl)-L-cysteic acid (I), N-(13-cis-Retinoyl)-L-cysteic acid (II), N-(all-trans-Retinoyl)-L-homocysteic acid (III), N-(13-cis-Retinoyl)-L-homocysteic acid (IV), N-(all-trans-Retinoyl)-L-cysteinesulfinic acid (V), and N-(13-cis-Retinoyl)-L-cysteinesulfinic acid (VI) have excellent solubility in the commercially available Taxol® preparation. It is thus possible to easily improve the conventional paclitaxel formulation using the inventive compounds. An ethanol solution is prepared of one of N-(all-trans-Retinoyl)-L-cysteic acid (I), N-(13-cis-Retinoyl)-L-cysteic acid (11), N-(all-trans-Retinoyl)-L-homocysteic acid (III), N-(13-cis-Retinoyl)-L-homocysteic acid (IV), N-(all-trans-Retinoyl)-L-cysteinesulfinic acid (V), or N-(13-cis-Retinoyl)-L-cysteinesulfinic acid (VI). The obtained solution is evaporated in vacuo to give waxy solid, whereupon Taxol® is added, dissolving the waxy solid. The Taxol® emulsion forms a liquid system with the compounds (I–VI) even at a molar ratio of paclitaxel to compound (I–VI) of more than 1:20.

Tests for evaluating the cytotoxicity of an improved paclitaxel formulation (Taxol® plus compound I–VI) at the molar ratios of paclitaxel:compound I (through compound VI) from 1:1 to 1:20, were carried out in cultures of human breast adenocarcinoma (the MDA-MB-231 cell line). The results of these tests are similar to the results obtained for the formulation paclitaxel and compound I (through VI) in saline. The extent of cell growth inhibition for this improved paclitaxel formulation (Taxol® and compound I–VI) at the molar ratio 1:10 was increased by almost 50% (compared to that of Taxol® alone).

The present invention thus exemplifies the inventive concept, that sparsely soluble therapeutic agents can be made more soluble, and their therapeutic efficacy potentiated, by presenting twelve new therapeutic formulations comprising the anticancer drug paclitaxel:

paclitaxel and N-(all-trans-Retinoyl)-L-cysteic acid in saline,
paclitaxel and N-(13-cis-Retinoyl)-L-cysteic acid in saline,
paclitaxel and V-(all-trans-Retinoyl)-L-homocysteic acid in saline,
paclitaxel and N-(13-cis-Retinoyl)-L-homocysteic acid in saline,
paclitaxel and N-(all-trans-Retinoyl)-L-cysteinesulfinic acid in saline,
pacditaxel and N-(13-cis-Retinoyl)-L-cysteinesulfinic acid in saline,
Taxol® and N-(all-trans-Retinoyl)-L-cysteic acid,
Taxol® and N-(13-cis-Retinoyl)-L-cysteic acid,
Taxol® and N-(all-trans-Retinoyl)-L-homocysteic acid,
Taxol® and N-(13-cis-Retinoyl)-L-homocysteic acid,
Taxol® and N-(all-trans-Retinoyl)-L-cysteinesulfinic acid, and
Taxol® and N-(13-cis-Retinoyl)-L-cysteinesulfinic acid.

These formulations showed both good physical and chemical stability, which is believed to reduce the effects connected with paclitaxel precipitation upon dilution. This is also believed to solve the issues related to the stringent requirements regarding facilities and vessels for preparation and storage of conventional paclitaxel preparations.

Notably, the compounds (I–VI) have low toxicity, but display significant cell growth inhibition, the effect increasing in the appropriate concentration ranges.

The results obtained by the present inventors have laid a foundation for the development of a technique for large-scale synthesis of the compounds (I–VI), pharmaceutically useful salts thereof, and in particular Na-salts thereof. The synthesis of the compounds (I–VI) of the invention involves a direct acylation of the amino groups of L-cysteic acid, L-homocysteic, and L-cysteinesulfinic acid by mixed carbonic-carboxylic acid anhydride in water-organic medium, containing $Na_2CO_3$. The solubility of the sodium salts of the compunds (I–VI) in 2-propanol-water mixtures make it possible to separate insoluble contaminants (inorganic salts and starting amino acids). The pure compounds (I–VI) are then obtained by precipitation from their concentrated solutions in 2-propanol-water using a methanol-2-propanol mixture.

The above method of synthesis developed by the inventors makes it possible to produce sodium salts of the compounds (I–VI) in good yields. The method is simple and timesaving. The final products can be prepared in pure form, without the need of chromatography. The compounds (I–VI) in the form of sodium salts can be stored in a solution of 2-propanol-water 2:1 (v/v) or ethanol-water 2:1 (v/v) for at least six months at low temperatures without any noticeable change in their properties. In order to prepare the formulations of the inventive compounds (I–VI) with paclitaxel or Taxol®, the sodium salts of these compounds are easily converted into the corresponding acidic forms, and dissolved in methanol.

Tests evaluating the cytotoxicity of the compounds I through VI, in the form of sodium salts in the concentration range $10^{-11}$ M to $10^{-6}$ M, have been performed in cultures of MDA-MB-231 cells, and revealed the following dependence: an increase of the concentrations of the inventive compounds led to an enhancement of cell growth inhibition, achieving a value close to 50% for compounds I and II; a value close to 35% for compounds III and IV; and a value close to 30% for compounds V and VI.

Sodium salts of the compounds I through VI were converted into the corresponding acidic forms of the compounds and dissolved in methanol, in order to prepare the formulations paclitaxel/compound (I–VI). At the same paclitaxel concentration, the formulation of paclitaxel and compound I, or paclitaxel and compound II, exhibited a high cell growth inhibition close to 70% (close to 45% compared to paclitaxel alone as positive control); the formulation of paclitaxel and compound III or paclitaxel and compound IV exhibited a cell growth inhibition close to 60% (close to 30% compared to paclitaxel alone as positive control); the formulation of paclitaxel and compound V or paclitaxel and compound VI exhibited a cell growth inhibition close to 55% (close to 25% compared to paclitaxel as positive control). The molar ratio of paclitaxel:compound (I–VI) was 1:7.

Sodium salts of the compounds (I–VI) were converted into the corresponding acidic forms of the compounds and dissolved in Taxol® to prepare the formulations Taxol®/compound (I–VI).

The extent of cell growth inhibition for the formulation of Taxol®/compound I or Taxol®/compound II was close to 75% (close to 50% compared to Taxol® alone as positive control); for the formulation Taxol®/compound III or Taxol®/compound IV, the inhibition was close to 65% (close to 35% compared to Taxol® alone as positive control); for formulation Taxol®/compound V or Taxol®/compound VI, close to 60% (close to 30% compared to Taxol® alone as positive control). The molar ratio of paclitaxel:compound (I–VI) was 1:10.

The compounds (I–VI) surprisingly combine an ability for growth inhibition of tumour cells with the power to dissolve paclitaxel, creating mixed micelles in saline. The inventors further show that these compounds (I–VI) are able potentiate the efficacy of paclitaxel. The present inventors have also developed a method of production and produced a lyophilized composition of compound (I–VI)/paclitaxel in mixed micellar systems.

The optimisation of mixed-micellar systems of compounds (I–VI)/paclitaxel was performed using different molar ratios of paclitaxel:compound (I–VI) and vehicle. The mixed-micellar systems according to the invention did not cause precipitation of the drug upon dilution 100 times and more in water solutions.

Solutions of paclitaxel and the compound (I–VI) in methanol were mixed at different molar ratios paclitaxel:compound (I–VI) equal to 1:3, 1:5, and 1:7. After evaporation of the organic solvent under reduced pressure, the resulting dried film was dissolved by the addition of distilled water or 0.05 M sodium acetate buffer, pH 5.6 or 10% solution of ethanol or 0.15 M solution of NaCl or 0.05 M sodium acetate buffer, pH 5.6 in 10% solution of ethanol to obtain a mixed-micellar solution of compound (I–VI)/paclitaxel. These solutions were filtered through a 0.22 μm sterile filter and stored at 4° C. All of these prototype systems produced significant antitumor activity in vitro for three weeks. No precipitation or other gross changes were observed during storage.

The mixed micelles did not appear to be very stable in solution. The preparations of compound (I–VI)/paclitaxel in mixed-micellar systems at the molar ratio paclitaxel compound (I–VI) of 1:7 were freeze-dried (as water solution, W or solution in 0.05 M sodium acetate buffer, pH 5.6, SAB) and stored in powder form during 6 months at 4° C. The preparations of compound (I–VI)/paclitaxel in mixed-micellar systems in dry form was shown to be stable for a sufficient period of time awaiting usage. There was no change in the concentration of the active ingredients at least during a 6-months storage at 4° C.

Upon reconstitution with either distilled water, or 0.05 M sodium acetate buffer, pH 5.6, or 10% ethanol, or 0.15 M solution of NaCl, or 0.05 M sodium acetate buffer, pH 5.6 in 10% ethanol, a clear solution was obtained immediately.

The preparations of the dried compound (I–VI)/paclitaxel in mixed-micellar systems (OF) which were reconstituted with 0.05 M sodium acetate buffer (W/SAB) or the ones that were freeze-dried as the solution in 0.05 M sodium acetate buffer and reconstituted with water (SAB/W) exhibit the best cytotoxic action on MDA-MB-231 cell line. The cytotoxic action was similar to that of compound (I–VI)/paclitaxel formulations in saline (Table 1):

TABLE 1

Cytotoxic action of formulations prepared according to the invention
Cell growth inhibition %

| Compounds | OF | | Formulation |
| --- | --- | --- | --- |
| | W/SAB | SAB/W | |
| I, II | close to 71 | close to 72 | close to 75 |
| III, IV | close to 62 | close to 63 | close to 60 |
| V, VI | close to 56 | close to 58 | close to 55 |

The inventive formulations compare favourably with Taxol®, but are believed to remove or alleviate the adverse effects associated to Cremophor® EL. Tests in vitro show remarkable results, and there are substantial grounds to believe that the pharmacological activity in human patients is improved, compared to that of conventional paclitaxel formulations. Consequently, the present invention makes available a method for preparing a water-soluble formulation of paclitaxel, comprising the steps of dissolving paclitaxel in a first solvent, dissolving a compound (I–VI) in a second solvent, mixing the aliquots of the resulting solutions of paclitaxel and the said compound in a desired molar ratio, and evaporating the resulting mixture to dryness.

Further, the invention makes available a method for preparation a water-soluble improved formulation of Taxol®, comprising the step of dissolving a compound (I–VI) in a solvent, evaporating the desired aliquot of the resulting solution to dryness and dissolving the residue in Taxol®.

Further, the invention makes available a method for preparation a stable storage formulation of paclitaxel, comprising the steps of dissolving paclitaxel in a first solvent, dissolving a compound (I–VI) in a second solvent, mixing the aliquots of the resulting solutions of paclitaxel and the said compound in a desired molar ratio.

Further, the invention makes available a method for preparing the formulation of paclitaxel for administration to a patient, comprising the steps of dissolving paclitaxel in a first solvent, dissolving a compound (I–VI) in a second solvent, mixing the aliquots of the resulting solutions of paclitaxel and the said compound in a desired molar ratio, evaporating the resulting mixture to dryness forming a residue of paclitaxel and the said compound, dissolving the said residue in a aqueous solution, lyophilisation of the solution formed, followed by reconstitution of the lyophilised product using a vehicle suitable for administration to a patient.

The invention will be illustrated in closer detail in the following non-limiting examples.

EXAMPLES

Materials and Methods all-trans-Retinoic, 13-cis-Retinoic, L-cysteic, L-homocysteic, and L-cysteinesulfinic acids were purchased from Sigma Chemical Co, St. Louis, Mo., USA. All other chemical reagents and solvents were purchased from Aldrich Chemical Co.

$^1$H-NMR spectra were determined at 400 MHz using a Varian Unity-400 spectrometer. Spectra were determinded for the acidic forms of the compounds, however the derivatives of L-homocysteic acid III and IV were used in the form of sodium salts. DMSO-$d_6$ was used as a solvent.

Merck silica gel 60 precoated plates were used for thin-layer chromatography (TLC) and developed in solvent system of chloroform:methanol:acetic acid:water (65:25:5:5, v/v/v/v). Detection of the compounds on TLC plates was achieved by spraying with 10% $H_2SO_4$ in methanol, heating to 150° C., or using a solution of 0, 3% ninhydrin in 1-butanol-acetic acid 100:3 (v/v).

The determination of the concentrations of the synthesized compounds was performed by UV-spectra (Shimadzu UV-mini-1240 spectrophotometer, $\lambda$÷250–500 nm, $\lambda_{max}$ 346 nm, $\epsilon$45000, MeOH) for the derivatives of all-trans-retinoic acid, and by weight for the derivatives of 13-cis-retinoic acid. The concentrations determined by UV-spectra were equal to the weights of the samples.

The compounds synthesized (in acidic form) are soluble in chloroform, THF, ethanol, methanol, and 70% aq ethanol. Sodium salts of the derivatives of L-cysteic and L-cysteinesulfinic acids (I, II, V, VI) are soluble only in mixtures containing water (e.g. methanol-water, ethanol-water, THF-water, etc). Sodium salts of the derivatives of L-homocysteic acid (III, IV) are also dissolved in methanol and some methanol containing mixtures (e.g. chloroform-methanol, THF-methanol, etc).

All steps of the synthesis were performed in dry nitrogen atmosphere.

Paclitaxel was purchased from Sigma (St. Louis, Mo., USA) and Taxol® was purchased from Bristol-Myers Squibb Co. Human breast adenocarcinoma MDA-MB-231 cell line was purchased from American Type Culture Collection (ATCC-HTB-26, Lot 1227150). The cell line was propagated by cultivation in Nunclon 25 cm$^2$ flasks (Nunc A/S, Denmark) in Minimum Essential Medium Eagle (MEM), containing antibiotics and supplemented with 10% (v/v) fetal bovine serum (FBS) (Sigma, St. Louis, Mo., USA). The cultures were maintained in growth medium at 37° C. in a humidified atmosphere, 95% air and 5% $CO_2$.

A suspension of tumour cells ($60 \times 10^3$ cells/mL) was prepared in MEM with 5% FBS and antibiotics. Cell suspension (200 µL) was seeded in wells of Nunclon 96-microwell plates (Nunc A/S, Denmark) at a density of $12 \times 10^3$ cell/well. The solutions of the drugs to be tested were added to the cultures on day 0 or day 1 in volumes of 2 µL. In all cases the cells were incubated for 3 days.

At the end of the incubation period, adherent cells were detached by trypsinization and the number of viable cells was counted using trypan blue dye exclusion test and a hemocytometer.

All experiments were performed at least twice and the cells counts were done in triplicate for each drug concentration. Each control and test series consisted of 6–8 cultures. The results are expressed as mean cell number ±SD and the differences between control and test series were evaluated by means of Student's t-test. The cytotoxicity of each tested drug was evaluated by the extent of cell growth inhibition. The Cell growth inhibition was evaluated as follows:

Cell growth inhibition, %= $\frac{\text{Control} - \text{Test Series}}{\text{Control}} \times 100$

Example 1

Synthesis of N-(all-trans-retinoyl)-L-cysteic acid all-trans-Retinoic acid (150 mg, 0.5 mmol) and triethylamine (71 µl, 0.51 mmol) were dissolved in 1 ml of anhydrous tetrahydrofuran, whereupon anhydrous acetonitrile (2 ml) was added, the mixture chilled to −20° C., and 66 µl (0.51 mmol) of butyl chloroformate added. After 30 min, the mixture, free of the precipitated triethylamine hydrochloride, was pipetted in a solution of L-cysteic acid monohydrate (140 mg, 0.75 mmol) in 3 ml of 1M $Na_2CO_3$ and 1.5 ml of $H_2O$. The mixture obtained was stirred for about 5 h at 20–25° C., acidified with 1 M $KHSO_4$ to pH 3–4 and filtered. The solution was extracted with chloroform-2-propanol-methanol (2:1:1, v/v/v, 15 ml) and concentrated under reduced pressure. The mixture of methanol-water (1:1, v/v, 15 ml) was added to the residue. The suspension obtained was washed with ether (2×10 ml), evaporated under reduced pressure, dissolved in 10 ml of methanol and filtered. After evaporation under reduced pressure, the residue was dissolved in 7 ml of anhydrous tetrahydrofuran, chilled to −20° C. and centrifuged (3000 rpm, −20° C., 20 min). The clear supernatant was evaporated under reduced pressure to give a yellow waxy solid. Yield: 40%.

$R_f$ 0.30–0.35. $^1$H-NMR (CD$_3$SOCD$_3$, 400 MHz) δ1.00 [6H, s, C(C$\underline{H}_3$)$_2$], 1.42 and 1.55 [2H+2H, 2m, C$\underline{H}_2$C$\underline{H}_2$C(CH$_3$)$_2$], 1.66 [3H, s, C$\underline{H}_3$C=CC(CH$_3$)$_2$], 1.94 [3H, s, (C$\underline{H}_3$C=(CH)$_3$C(CH$_3$)=CHCO], 2.00 (2H, m, C$\underline{H}_2$C=), 2.25 (3H, s, C$\underline{H}_3$C=CHCO), 2.79–2.90 (2H, m, SC$\underline{H}_2$), 4.40 (1H, m, NC$\underline{H}$), 5.84 (1H, s, =C$\underline{H}$CO), 6.10–6.35 [4H, m, C$\underline{H}$=C$\underline{H}$C(CH$_3$)=C$\underline{H}$C$\underline{H}$=C$\underline{H}$], 6.91 (1H, dd, J15.2, 11.5 Hz, CHCH=C$\underline{H}$), 8.08 (1H, d, J6.4 Hz, N$\underline{H}$), ~12.4 (1H, br s, CO$_2\underline{H}$).

Example 2

Evaluation of the Cytotoxicity of Compound I in Cultures of Human Breast Adenocarcinoma MDA-MB-231 Cell Line, Related to the Initial Concentration of Compound I in Saline Before Adding to Medium for Dilution Initial solutions of compound I in concentrations from 0.005 to 5.0 mg/ml were prepared by dissolving the dry substance in saline. Saline solutions of compound I were prepared having the following concentrations: 0.005, 0.05, 0.5, 1.0 and 5.0 mg/ml. From these solutions, working solutions in MEM with 5% FBS for adding to cultures were prepared in the concentration of 4 mM.

Cultures of MDA-MB-231 cell line were treated with solutions of compound I after cell sowing on day 1. Aliquots of the working solutions (2 µL) were added to 200 µL cultures to a final concentration of 40 nM in the cultures. In the control cultures, 2 µL of medium with 5% FBS were added as solvent control. After cultivation for two consecutive days, the number of living cells in cultures was counted, and the extent of growth inhibition of MDA-MB-231 cell line was calculated for evaluating the cytotoxicity of the tested solutions of compound I.

After three days of cultivation the control cultures contained $(49.9 \pm 3.85) \times 10^3$ cells.

The cultures, treated with solutions of compound I had the following number of living cells:

| | |
|---|---|
| 0.005 mg/mL: | $(33.3 \pm 2.55) \times 10^3$, cell growth inhibition 33.3% ($p < 0.01$); |
| 0.05 mg/mL: | $(33.9 \pm 2.78) \times 10^3$, cell growth inhibition 32.1% ($p < 0.01$); |
| 0.5 mg/mL: | $(34.2 \pm 5.09) \times 10^3$, cell growth inhibition 31.5% ($p < 0.05$); |
| 1.0 mg/mL: | $(30.8 \pm 3.53) \times 10^3$, cell growth inhibition 38.3% ($p < 0.01$); |
| 5.0 mg/mL: | $(36.1 \pm 4.10) \times 10^3$, cell growth inhibition 27.7% ($p < 0.05$). |

It is thus shown, that compound I (in a concentration of 40 nM) exerts a significant cytotoxic action in cultures of human breast adenocarcinoma (the MDA-MB-231 cell line). A more pronounced cytotoxic action is displayed by the solution, prepared from an initial saline solution of compound I in a concentration of 1 mg/mL. In this case the extent of cell growth inhibition was 38.3% ($p < 0.01$).

Example 3

Evaluation of the Cytotoxicity of Compound I in Cultures of Human Breast Adenocarcinoma MDA-MB-231 Cell Line, Related to Final Concentration of Compound I in Cultures An initial stock saline solution of compound I (1 mg/ml) was prepared by dissolving the dry substance in saline. From this solution, the working solutions of compound I in MEM with 5% FBS were prepared in different concentrations for adding to cultures, by means of consecutive dilutions.

Cultures of MDA-MB-231 cells were treated with drug solutions in MEM, containing 5% FBS, after sowing on day 1. Aliquots of the working solutions (2 µL) with different concentrations of compound I were added to 200 µL cultures to final concentrations of compound I from $10^{-11}$ to $10^{-6}$ mol/L in cultures. In the control cultures, 2 µL of medium with 5% FBS was added as solvent control. After cultivation for two consecutive days, the number of living cells in cultures was counted and the extent of growth inhibition of MDA-MB-231 cells calculated for evaluation of the cytotoxicity of the tested solutions of compound I.

After three days of cultivation, the control cultures contained $(49.9 \pm 3.85) \times 10^3$ cells.

Cultures, treated with solutions of compound I had the following number of living cells:

| | |
|---|---|
| $10^{-11}$ mol/L: | $(36.3 \pm 3.82) \times 10^3$, cell growth inhibition 27.3% ($p < 0.05$); |
| $10^{-10}$ mol/L: | $(40.6 \pm 1.69) \times 10^3$, cell growth inhibition 18.6% ($p < 0.05$); |
| $10^{-9}$ mol/L: | $(40.0 \pm 2.31) \times 10^3$, cell growth inhibition 19.8% ($p < 0.05$); |
| $10^{-8}$ mol/L: | $(35.0 \pm 4.38) \times 10^3$, cell growth inhibition 29.9% ($p < 0.05$); |
| $4 \times 10^{-8}$ mol/L: | $(30.9 \pm 1.62) \times 10^3$, cell growth inhibition 38.1% ($p < 0.001$); |
| $10^{-7}$ mol/L: | $(30.4 \pm 1.83) \times 10^3$, cell growth inhibition 39.1% ($p < 0.001$); |
| $10^{-6}$ mol/L: | $(28.9 \pm 2.68) \times 10^3$, cell growth inhibition 42.1% ($p < 0.001$). |

It is thus shown, that compound I exerts a significant cytotoxic action against human breast adenocarcinoma cells. The extent of cell growth inhibition can be increased to 42.1% ($p < 0.001$) by increasing the concentration of compound I.

Example 4

Comparative Cytotoxicity Testing of Paclitaxel, Taxol®, the Formulation of Paclitaxel-compound I, and Compound I Alone in Cultures of Human Breast Adenocarcinoma (MDA-MB-231 Cell Line)

A stock solution of paclitaxel was prepared in ethanol. The solutions of Taxol®, the formulation of paclitaxel-compound I, and compound I were prepared in saline. A working solution of each drug in MEM with 5% FBS were prepared in following concentrations for adding to cultures:

| | |
|---|---|
| Formulation: | $8 \times 10^{-7}$ mol/L of paclitaxel and $4 \times 10^{-6}$ mol/L of compound I |
| Compound I: | $4 \times 10^{-6}$ mol/L |
| Paclitaxel: | $8 \times 10^{-7}$ mol/L |
| Taxol ®: | $8 \times 10^{-7}$ mol/L of paclitaxel |

Cultures of MDA-MB-231 cells were treated with the drug solutions in MEM, containing 5% FBS, after sowing on day 0. Aliquots of the working solutions (2 µl) were added to 200 µl cultures to final concentrations of drugs in cultures:

| | |
|---|---|
| Formulation: | $8 \times 10^{-9}$ mol/L of paclitaxel and $4 \times 10^{-8}$ mol/L of compound I |
| Compound I: | $4 \times 10^{-8}$ mol/L |
| Paclitaxel: | $8 \times 10^{-9}$ mol/L |
| Taxol ®: | $8 \times 10^{-9}$ mol/L of paclitaxel |

In the control cultures, 2 µl of medium with 5% FBS were added as solvent control. After cultivation for three consecutive days the number of living cells in cultures was counted and extent of growth inhibition of MDA-MB-231 cells was calculated for evaluating the cytotoxicity of each tested drug.

The control cultures contained $(27.0 \pm 3.79) \times 10^3$ cells.

The cultures treated with drugs had the following number of living cells:

| | |
|---|---|
| Formulation: | $(8.1 \pm 0.65) \times 10^3$, cell inhibition 70% ($p < 0.001$) |
| Compound I: | $(16.3 \pm 2.50) \times 10^3$, cell inhibition 39.6% ($p < 0.05$) |
| Paclitaxel: | $(15.5 \pm 1.63) \times 10^3$, cell inhibition 42.6% ($p < 0.02$) |
| Taxol®: | $(14.7 \pm 2.33) \times 10^3$, cell inhibition 45.6% ($p < 0.02$) |

It was thus shown, that the formulation of paclitaxel and component I exerts a significant cytotoxic effect against human breast adenocarcinoma cells, exceeding both that of Taxol® (positive control) and paclitaxel alone. The growth inhibition of MDA-MB-231 cells with reference to Taxol® was 45% (p<0,02). The cytotoxic action of compound I alone was 39.6% (p<0.05).

Example 5

Evaluation of the Cytotoxicity of the Formulation Paclitaxel-compound 1 in Cultures of Human Breast Adenocarcinoma MDA-MB-231 Cell Line, Related to the Molar Ratio of Paclitaxel:compound I Initial solutions of the formulation in saline at the molar ratios paclitaxel/compound I 1:3, 1:4, 1:5, 1:6, 1:7 and 1:10 were prepared. From these solutions, the working solutions in MEM with 5% FBS for adding to cultures were prepared. The concentration of paclitaxel was equal to $10^{-6}$ M.

Cultures of MDA-MB-231 cells were treated with drug solutions in MEM, containing 5% FBS, after sowing on day 1. Aliquots of the working solutions (2 μL) were added to 200 μL cultures to final concentration of paclitaxel in cultures equal to $10^{-8}$ M. In the control cultures, 2 μL of medium with 5% FBS were added as solvent control. After cultivation for two consecutive days, the number of living cells in the cultures was calculated for evaluation of the cytotoxicity of the tested solutions of the formulation.

After three days of cultivation, the control cultures contained $(54.8 \pm 3.53) \times 10^3$ cells.

Cultures, treated with paclitaxel at the concentration 10 nM, contained $(37.6 \pm 2.12) \times 10^3$ cells, and exhibited a cell growth inhibition of 31.4% (p<0.001).

Cultures, treated with solutions of the formulation at the molar ratio paclitaxel/compound I equal to 1:3, 1:4, 1:5, 1:6, 1:7 and 1:10 in medium with 5% FBS, had the following number of living cells:
1:3: $(25.7 \pm 1.46) \times 10^3$, the cell growth inhibition being 53.1% (p<0.001), and the cell growth inhibition compared to that of paclitaxel was increased by 31.6% (p<0.001);
1:4: $(28.0 \pm 1.78) \times 10^3$, the cell growth inhibition being 48.9% (p<0.001), and the ell growth inhibition compared to that of paclitaxel was increased by 25.5% (p<0.01);
1:5: $(22.8 \pm 2.13) \times 10^3$, the cell growth inhibition being 58.4% (p<0.001), and the cell growth inhibition compared to that of paclitaxel was increased by 39.4% (p<0.001);
1:6: $(21.7 \pm 1.52) \times 10^3$, the cell growth inhibition being 60.4% (p<0.001), and the cell growth inhibition compared to that of paclitaxel was increased by 42.3% (p<0.001);
1:7: $(21.6 \pm 1.81) \times 10^3$, the cell growth inhibition being 60.6% (p<0.001), and the cell growth inhibition compared to that of paclitaxel was increased by 42.6% (p<0.001);
1:10: $(20.3 \pm 1.21) \times 10^3$, the cell growth inhibition being 63.0% (p<0.001), and the cell growth inhibition compared to that of paclitaxel was increased by 46.0% (p<0.001).

Example 6

Comparative Cytotoxicity Testing of Taxol® and an Improved Formulation (Taxol® Plus Compound I) in Cultures of Human Breast Adenocarcinoma MDA-MB-231 Cell Line, Related to the Molar Ratios of Paclitaxel to Compound I Initial solutions of the inventive formulation at the molar ratios paclitaxel to compound I equal to 1:1, 1:3, 1:6, 1:10, 1:15 and 1:20 were prepared. From these solutions, the working solutions in MEM with 5% FBS for adding to cultures were prepared. The concentration of paclitaxel was equal to 16M.

Cultures of MDA-MB-231 cells were treated with drug solutions in MEM, containing 5% FBS, after sowing on day 1. Aliquots of the working solutions (2 μL) were added to 200 μL cultures, to a final concentration of paclitaxel in the cultures equal to $10^{-8}$ M. In the control cultures, 2 μL of medium with 5% FBS were added as solvent control. After cultivation for two consecutive days, the number of living cells in the cultures was calculated for evaluation of the cytotoxicity of the tested solutions.

After three days of cultivation, the control cultures contained $(52.3 \pm 2.78) \times 10^3$ cells.

Cultures, treated with Taxol® in a concentration of 10 nM paclitaxel, contained $(32.5 \pm 2.04) \times 10^3$ cells, and exhibited a cell growth inhibition of 37.9% (p<0.001).

Cultures, treated with solutions of the inventive formulation (Taxol®+compound I) at the molar ratio paclitaxel/compound I equal to 1:1, 1:3, 1:6, 1:10, 1:15 and 1:20, in medium with 5% FBS, had the following number of living cells:
1:1: $(26.9 \pm 1.60) \times 10^3$, the cell growth inhibition being 48.6% (p<0.001), and the cell growth inhibition compared to that of Taxol® was increased by 17.2% (p<0.05);
1:3: $(22.2 \pm 1.79) \times 10^3$, the cell growth inhibition being 57.6% (p<0.001), and the cell growth inhibition compared to that of Taxol® was increased by 31.7% (p<0.002);
1:6: $(17.5 \pm 1.34) \times 10^3$, the cell growth inhibition being 66.5% (p<0.001), and the cell growth inhibition compared to that of Taxol® was increased by 46.2% (p<0.001);
1:10: $(15.8 \pm 1.38) \times 10^3$, the cell growth inhibition being 69.8% (p<0.001), and the cell growth inhibition compared to that of Taxol® was increased by 51.4% (p<0.001);
1:15: $(15.1 \pm 1.47) \times 10^3$, the cell growth inhibition being 71.1% (p<0.001), and the cell growth inhibition compared to that of Taxol® was increased by 53.5% (p<0.001);
1:20: $(14.4 \pm 1.16) \times 10^3$, the cell growth inhibition being 72.5% (p<0.001), and the cell growth inhibition compared to that of Taxol® was increased by 55.7% (p<0.001).

Example 7

Synthesis of N-(13-cis-retinoyl)-L-cysteic acid 13-cis-Retinoic acid (150 mg, 0.5 mmol) and triethylamine (71 μl, 0.51 mmol) were dissolved in 1 ml of anhydrous tetrahydrofuran, whereupon anhydrous acetonitrile (2 ml) was added, the mixture chilled to −20° C., and 66 μl (0.51 mmol) of butyl chloroformate added. After 30 min, the mixture, free of the precipitated triethylamine hydrochloride, was pipetted into a solution of L-cysteic acid monohydrate (140 mg, 0.75 mmol) in 3 ml of 1M $Na_2CO_3$ and 1.5 ml of $H_2O$. The mixture obtained was stirred for about 5 h at 20–25° C., acidified with 1 M $KHSO_4$ to pH 3–4 and filtered. The solution was extracted with chloroform-2-propanol-methanol (2:1:1, v/v/v, 15 ml) and concentrated under reduced pressure. The mixture of methanol-water (1:1, v/v, 15 ml) was added to the residue. The suspension obtained was washed with ether (2×10 ml), evaporated under reduced pressure, dissolved in 10 ml of methanol and filtered. After evaporation under reduced pressure, the residue was dissolved in 7 ml of anhydrous tetrahydrofuran, chilled to −20° C. and centrifuged (3000 rpm, −20° C., −20 min). The clear supernatant was evaporated under reduced pressure to give yellow waxy solid.

Yield: 30%.

$R_f$ 0.30–0.35. $^1$H-NMR (CD$_3$SOCD$_3$, 400 MHz) δ 1.00 [6H, s, C(C$\underline{H}_3$)$_2$], 1.42 and 1.57 [2H+2H, 2m, C$\underline{H}_2$C$\underline{H}_2$C(CH$_3$)$_2$], 1.67 [3H, s, C$\underline{H}_3$C=CC(CH$_3$)$_2$], 1.95–1.97 (3H+3H, 2s, C$\underline{H}_3$C=(CH)$_3$C(C$\underline{H}_3$)=CHCO], 1.99 (2H, m, C$\underline{H}_2$C=), 2.83 (2H, m SC$\underline{H}_2$), 4.38 (1H, m, NC$\underline{H}$), 5.68 (1H, s, =C$\underline{H}$CO), 6.12–6.26 [3H, m, C$\underline{H}$=C$\underline{H}$C(CH$_3$)=C$\underline{H}$CH=CH], 6.87 (1H, dd, J 15.4, 11.4 Hz, CHC$\underline{H}$=CH), 7.85 [1H, d, J 15.4 Hz, CH=CHC(CH$_3$)=CHCH=C$\underline{H}$], 8.03 (1H, d, J6.4 Hz, N$\underline{H}$), 12.4 (1H, br s, CO$_2\underline{H}$).

Example 8

Evaluation of the Cytotoxicity of Compound II in Cultures of Human Breast Adenocarcinoma MDA-MB-231 Cell Line, Related to the Initial Concentration of Compound II in Saline Before Addition to Medium for Dilution Initial solutions of compound II in concentrations from 0.005 to 5.0 mg/ml were prepared by dissolving the dry substance in saline. Saline solutions of compound II were prepared, having the following concentrations: 0.005, 0.05, 0.5, 1.0 and 5.0 mg/ml. From these solutions, working solutions in MEM with 5% FBS for adding to cultures were prepared in a concentration of 4 mM.

Cultures of MDA-MB-231 cell line were treated with solutions of compound II after sowing on day 1. Aliquots of the working solutions (2 μL) were added to 200 μL cultures to a final concentration of 40 nM in the cultures. In the control cultures 2 μL of medium with 5% FBS were added as solvent control. After cultivation for two consecutive days the number of living cells in cultures was counted and the extent of growth inhibition of MDA-MB-231 cell line was calculated for evaluation of the cytotoxicity of the tested solutions of compound II.

After three days of cultivation the control cultures contained $(51.6\pm3.46)\times10^3$ cells. The cultures, treated with solutions of compound II had the following number of living cells:

| | |
|---|---|
| 0.005 mg/ml: | $(34.8 \pm 3.27) \times 10^3$, cell growth inhibition 32.6% ($p < 0.01$); |
| 0.05 mg/ml: | $(33.4 \pm 2.91) \times 10^3$, cell growth inhibition 35.3% ($p < 0.002$); |
| 0.5 mg/ml: | $(33.1 \pm 3.01) \times 10^3$, cell growth inhibition 35.9% ($p < 0.002$); |
| 1.0 mg/ml: | $(32.2 \pm 2.14) \times 10^3$, cell growth inhibition 37.6% ($p < 0.001$); |
| 5.0 mg/ml: | $(36.5 \pm 3.88) \times 10^3$, cell growth inhibition 29.3% ($p < 0.02$). |

It is thus shown, that compound II—at a concentration of 40 nM—exerts significant cytotoxic action in cultures of human breast adenocarcinoma MDA-MB-231 cell line. A more pronounced cytotoxic action is displayed by the solution, prepared from initial saline solution of compound II in concentration of 1 mg/mL. In this case the extent of cell growth inhibition was 37.6% ($p<0.001$).

Example 9

Evaluation of the Cytotoxicity of Compound II in Cultures of Human Breast Adenocarcinoma MDA-MB-231 Cell Line, Related to the Final Concentration of Compound II in Cultures Initial stock saline solution of compound II (1 mg/ml) was prepared by dissolving of the dry substance in saline. From this solution, the working solutions of compound II in MEM with 5% FBS were prepared in different concentrations by means of consecutive dilutions for adding to the cultures.

Cultures of MDA-MB-231 cells were treated with drug solutions in MEM, containing 5% FBS, after sowing on day 1. Aliquots of working solutions (2 μL) with different concentrations of compound II were added to 200 μL cultures to final concentrations of compound II from $10^{-11}$ to $10^{-6}$ mol/L in cultures. In control cultures 2 μL of medium with 5% FBS were added as solvent control. After cultivation for two consecutive days the number of living cells in cultures was counted and the extent of growth inhibition of MDA-MB-231 cells was calculated for evaluating the cytotoxicity of tested solutions of compound II.

After three days of cultivation the control cultures contained $(51.6\pm3.46)\times10^3$ cells.

Cultures, treated with solutions of compound II had the following number of living cells:

| | |
|---|---|
| $10^{-11}$ mol/L: | $(36.7 \pm 3.65) \times 10^3$, cell growth inhibition 28.9% ($p < 0.02$); |
| $10^{-10}$ mol/L: | $(42.4 \pm 1.93) \times 10^3$, cell growth inhibition 17.8% ($p < 0.05$); |
| $10^{-9}$ mol/L: | $(40.5 \pm 2.11) \times 10^3$, cell growth inhibition 21.5% ($p < 0.02$); |
| $10^{-8}$ mol/L: | $(37.4 \pm 3.86) \times 10^3$, cell growth inhibition 27.5% ($p < 0.02$); |
| $4 \times 10^{-8}$ mol/L: | $(32.6 \pm 2.52) \times 10^3$, cell growth inhibition 36.8% ($p < 0.001$); |
| $10^{-7}$ mol/L: | $(31.8 \pm 2.05) \times 10^3$, cell growth inhibition 38.4% ($p < 0.001$); |
| $10^{-6}$ mol/L: | $(30.0 \pm 2.14) \times 10^3$, cell growth inhibition 41.9% ($p < 0.001$). |

Thus compound II is shown to exert a significant cytotoxic action against human breast adenocarcinoma cells. The extent of cell growth inhibition increases with increasing concentration of compound II up to 41.9% ($p<0.001$).

Example 10

Comparative Cytotoxicity Testing of Paclitaxel, Taxol®, the Formulation Paclitaxel-compound II and Compound II in Cultures of Human Breast Adenocarcinoma MDA-MB-231 Cell Line A stock solution of paclitaxel was prepared in ethanol. The solutions of Taxol®, the formulation of paclitaxel-compound II and compound II were prepared in saline. A working solution of each drug in MEM with 5% FBS was prepared in the following concentrations for adding to the cultures:

| | |
|---|---|
| Formulation: | $8 \times 10^{-7}$ mol/L of paclitaxel and $4 \times 10^{-6}$ mol/L of compound II |
| Compound II: | $4 \times 10^{-6}$ mol/L |
| Paclitaxel: | $8 \times 10^{-7}$ mol/L |
| Taxol® : | $8 \times 10^{-7}$ mol/L of paclitaxel |

Cultures of MDA-MB-231 cells were treated with drug solutions in MEM, containing 5% FBS, after sowing on day 0. Aliquots of the working solutions (2 μl) were added to 200 μl cultures to a final concentration of drugs in the cultures:

| | |
|---|---|
| Formulation: | $8 \times 10^{-9}$ mol/L of paclitaxel and $4 \times 10^{-8}$ mol/L of compound II |
| Compound II: | $4 \times 10^{-8}$ mol/L |
| Paclitaxel: | $8 \times 10^{-9}$ mol/L |
| Taxol®: | $8 \times 10^{-9}$ mol/L of paclitaxel |

In the control cultures, 2 µl of medium with 5% FBS was added as solvent control. After cultivation for three consecutive days, the number of living cells in cultures was counted and the extent of growth inhibition of MDA-MB-231 cells calculated for evaluation the cytotoxicity of each tested drug.

The control cultures contained $(46.2\pm4.14)\times10^3$ cells. The cultures treated with the drugs had the following number of living cells:

| | |
|---|---|
| Formulation: | $(14.7 \pm 2.61) \times 10^3$, cell growth inhibition 68.2% ($p < 0.001$); |
| Compound II: | $(29.9 \pm 2.38) \times 10^3$, cell growth inhibition 35.3% ($p < 0.01$); |
| Paclitaxel: | $(26.3 \pm 1.96) \times 10^3$, cell growth inhibition 43.1% ($p < 0.002$) |
| Taxol®: | $(25.5 \pm 2.15) \times 10^3$, cell growth inhibition 44.8% ($p < 0.001$). |

This shows that the formulation paclitaxel-component II exerts a significant cytotoxic effect against human breast adenocarcinoma cells, exceeding that of Taxol® (positive control) and paclitaxel. The growth inhibition of MDA-MB-231 cells compared to that of Taxol® was increased by 42.4% (p<0,01). The cytotoxic action of compound II alone was 35.3% (p<0.01).

Example 11

Evaluation of the Cytotoxicity of Paclitaxel-compound II in Cultures on Human Breast Adenocarcinoma MDA-MB-231 Cell Line, Related to the Molar Ratios of Paclitaxel/compound II Initial solutions of the formulation in saline at molar ratios paclitaxel:compound II equal to 1:3, 1:4, 1:5, 1:6, 1:7 and 1:10 were prepared. From these solutions the working solutions in MEM with 5% FBS for adding to cultures were prepared. The concentration of paclitaxel was equal to $10^{-6}$ M.

Cultures of MDA-MB-231 cells were treated with drug solutions in MEM, containing 5% FBS, after sowing on day 1. Aliquots of the working solutions (2 µL) were added to 200 µL cultures to final concentration of paclitaxel in cultures equal to $10^{-8}$ M. In control cultures 2 µL of medium with 5% FBS was added as solvent control. After cultivation for two consecutive days, the number of living cells in cultures was calculated for evaluating the cytotoxicity of the tested solutions of the formulation.

After three days of cultivation the control cultures contained $(53.2\pm2.84)\times10^3$ cells.

Cultures, treated with paclitaxel in a concentration of 10 nM, contained $(32.1\pm1.29)\times10^3$ cells, the cell growth inhibition was thus 39.7% (p<0.001);

Cultures, treated with solutions of the formulation at the molar ratio paclitaxel to compound II equal to 1:3, 1:4, 1:5, 1:6, 1:7 and 1:10 in medium with 5% FBS, had the following number of living cells:

1:3: $(22.4\pm2.75)\times10^3$, the cell growth inhibition being 57.9% (p<0.001), and the cell growth inhibition compared to that of paclitaxel was increased by 30.2% (p<0.01);

1:4: $(21.3\pm2.46)\times10^3$, the cell growth inhibition being 60.0% (p<0.001), and the cell growth inhibition compared to that of paclitaxel was increased by 33.6% (p<0.01);

1:5: $(19.8\pm2.37)\times10^3$, the cell growth inhibition being 62.8% (p<0.001), and the cell growth inhibition compared to that of paclitaxel was increased by 38.3% (p<0.001);

1:6: $(18.7\pm2.03)\times10^3$, the cell growth inhibition being 64.8% (p<0.001), and the cell growth inhibition compared to that of paclitaxel was increased by 41.7 (p<0.001);

1:7: $(18.1\pm1.89)\times10^3$, the cell growth inhibition being 66.0% (p<0.001), and the cell growth inhibition compared to that of paclitaxel was increased by 43.6% (p<0.001);

1:10: $(17.5\pm1.24)\times10^3$, the cell growth inhibition being 67.1% (p<0.001), and the cell growth inhibition compared to that of paclitaxel was increased by 45.5% (p<0.001).

Example 12

Comparative Cytotoxicity Testing of Taxol® and the Inventive Formulation (Taxol®+Compound II) in Cultures of Human Breast Adenocarcinoma MDA-MB-231 Cell Line, Related to the Molar Ratios Paclitaxel to Compound II Initial solutions of the inventive formulation at the molar ratios of paclitaxel to compound II equal to 1:1, 1:3, 1:6, 1:10, 1:15 and 1:20 were prepared. From these solutions the working solutions in MEM with 5% FBS were prepared for adding to cultures. The concentration of paclitaxel was equal to $10^{-6}$ M.

Cultures of MDA-MB-231 cells were treated with drug solutions in MEM, containing 5% FBS, after sowing on day 1. Aliquots of the working solutions (2 µL) were added to 200 µL cultures to a final concentration of paclitaxel in the cultures equal to $10^{-8}$ M. In the control cultures, 2 µL of medium with 5% FBS was added as solvent control. After cultivation for two consecutive days, the number of living cells in cultures was calculated for evaluating the cytotoxicity of the tested solutions.

After three days of cultivation, the control cultures contained $(48.7\pm3.12)\times10^3$ cells.

Cultures, treated with Taxol® in a concentration of 10 nM paclitaxel, contained $(29.5\pm2.68)\times10^3$ cells, and the cell growth inhibition was 39.4% (p<0.001);

Cultures, treated with solutions of the inventive formulation (Taxol®+compound II) at the molar ratio paclitaxel:compound II equal to 1:1, 1:3, 1:6, 1:10, 1:15, and 1:20 in medium with 5% FBS, had the following number of living cells:

1:1: $(19.4\pm2.37)\times10^3$, the cell growth inhibition being 60.2% (p<0.001), and the cell growth inhibition compared to that of Taxol® was increased by 34.2% (p<0.02);

1:3: $(18.2\pm2.28)\times10^3$, the cell growth inhibition being 62.6% (p<0.001), and the cell growth inhibition compared to that of Taxol® was increased by 38.3% (p<0.01);

1:6: $(16.0\pm2.03)\times10^3$, the cell growth inhibition being 67.1% (p<0.001), and the cell growth inhibition compared to that of Taxol® was increased by 45.8% (p<0.002);

1:10: $(14.9\pm1.81)\times10^3$, the cell growth inhibition being 69.4% (p<0.001), and the cell growth inhibition compared to that of Taxol® was increased by 49.5% (p<0.001);

1:15: $(14.2\pm1.85)\times10^3$, the cell growth inhibition being 70.8% (p<0.001), and the cell growth inhibition compared to that of Taxol® was increased by 51.9% (p<0.001);

1:20: $(13.6\pm1.59)\times10^3$, the cell growth inhibition being 72.1% (p<0.001), and the cell growth inhibition compared to that of Taxol® was increased by 53.9% (p<0.001).

Example 13

Synthesis of N-(all-trans-retinoyl)-L-cysteic Acid (Sodium Salt) (I)

All-trans-Retinoic acid (150 mg, 0.5 mmol) and triethylamine (71 µL, 0.51 mmol) were dissolved in 1 ml anhydrous tetrahydrofuran, then anhydrous acetonitrile (2 ml) was added, the mixture chilled to −20° C., and 66 µl (0.51 mmol) of isobutyl chloroformate added. After 30 min, the mixture, free of the precipitated triethylamine hydrochloride, was pipetted in a solution of L-cysteic acid monohydrate (94 mg, 0.5 mmol) in 3 ml of 1M $Na_2CO_3$ and 1.5 ml of $H_2O$. The mixture obtained was stirred for about 5 h at 20–25° C., diluted with 15 ml of 2-propanol-water 2:1 (v/v), filtered and concentrated under reduced pressure to approximately 5 ml. 20 ml of 2-propanol-water 5:1 (v/v) was then added, and the solution shaken during a few minutes while a white precipitate was formed. The suspension obtained was filtered, concentrated as described above, and diluted with 20 ml of 2-propanol-methanol 1:1 (v/v). A yellow precipitate of the desired product was separated, dissolved in 15 ml of 2-propanol-water 2:1 (v/v) and stored overnight at −18° C. in order to remove traces of impurities. After removal of insoluble material, a clear solution of pure product was obtained. This solution was used for storage of compound I.

Yield: 40%.

$R_f$ 0.30–0.35. $^1$H-NMR ($CD_3SOCD_3$, 400 MHz) δ1.00 [6H, s, C(CH$_3$)$_2$], 1.43 and 1.56 [2H+2H, 2m, CH$_2$C H$_2$C(CH$_3$)$_2$], 1.67 [3H, s, CH$_3$C=CC(CH$_3$)$_2$], 1.95 [3H, s, CH$_3$C=(CH)$_3$C(CH$_3$)=CHCO], 1.99 (2H, m, CH$_2$C=), 2.25 (3H, s, CH$_3$C=CHCO), 2.75–2.89 (2H, m, SCH$_2$), 4.40 (1H, m, NCH), 5.84 (1H, s, =CHCO), 6.11–6.36 [4H, m, CH=CHC(CH$_3$)=CHCH=CH], 6.91 [1H, dd, J 15.2, 11.5 Hz, CH=CHC(CH$_3$)=CHCH=CH], 8.07 (1H, d, J6.4 Hz, NH), ~12.4 (1H, br s, CO$_2$H).

In order to obtain the acidic form of compound I, a solution of the compound (2-propanol-water 2:1, v/v) was evaporated under reduced pressure, dissolved in water, carefully acidified with 0.1M HCl to pH 3.5 and extracted with chloroform-2-propanol-methanol (2:1:1, v/v/v). After evaporation of organic solvents under reduced pressure, the residue was dissolved in dry methanol (approximately 5 mg/mL), stored overnight at −18° C., filtered and immediately used.

Example 14

Synthesis of N-(13-cis-retinoyl)-L-cysteic acid (Sodium Salt) (II)

This compound was synthesized as described above for I, using 150 mg (0.5 mmol) of 13-cis-retinoic acid and 94 mg (0.5 mmol) of L-cysteic acid monohydrate.

Yield: 35%.

$R_f$ 0.30–0.35. $^1$H-NMR ($CD_3SOCD_3$, 400 MHz) δ1.00 [6H, s, C(CH$_3$)$_2$], 1.43 and 1.57 [2H+2H, 2m, CH$_2$C H$_2$C(CH$_3$)$_2$], 1.67 [3H, s, CH$_3$C=CC(CH$_3$)$_2$], 1.95 and 1.98 (3H+3H, 2s, CH$_3$C=(CH)$_3$C(CH$_3$)=CHCO], 1.99 (2H, m, CH$_2$C=), 2.82 (2H, m, SCH$_2$), 4.37 (1H, m, NCH), 5.68 (1H, s, =CHCO), 6.13–6.26 [3H, m, CH=CHC(CH$_3$)=C HCH=CH], 6.87 [1H, dd, J 15.4, 11.4 Hz, CH=CHC(CH$_3$) =CHCH=CH], 7.85 [1H, d, J 15.4 Hz, CH=CHC(CH$_3$) =CHCH=CH], 8.04 (1H, d, J6.4 Hz, NH), 12.4 (1H, br s, CO$_2$H).

Example 15

Synthesis of N-(all-trans-retinoyl)-L-homocysteic Acid (Sodium Salt) (III)

This compound was synthesized as described above for I, using 150 mg (0.5 mmol) of all-trans-retinoic acid and 92 mg (0.5 mmol) of L-homocysteic acid.

Yield: 31%.

$R_f$ 0.30–0.35. $^1$H-NMR ($CD_3SOCD_3$, 400 MHz) δ1.00 [6H, s, C(CH$_3$)$_2$], 1.43 and 1.56 [2H+2H, 2m, CH$_2$C H$_2$C(CH$_3$)$_2$], 1.67 [3H, s, CH$_3$C=CC(CH$_3$)$_2$], 1.87 (2H, m, SCH$_2$CH$_2$), 1.94 [3H, s, CH$_3$C=(CH)$_3$C(CH$_3$)=CHCO], 1.99 (2H, m, CH$_2$C=), 2.25 (3H, s CH$_3$C=CHCO), 2.41 (2H, m, SCH$_2$), 3.94 (1H, m, NCH), 5.98 (1H, s, =CHCO), 6.11–6.32 [4H, m, CH=CHC(CH$_3$)=CHCH=C], 6.86 (1H, dd, J 15.0, 11.5 Hz, =CHCH=CH), 7.43 (1H, d, J7.1 Hz, NH).

Example 16

Synthesis of N-(13-cis-retinoyl)-L-homocysteic Acid (Sodium Salt) (IV)

This compound was synthesized as described above for I, using 150 mg (0.5 mmol) of 13-cis-retinoic acid and 92 mg (0.5 mmol) of L-homocysteic acid.

Yield: 25%.

$R_f$ 0.30–0.35. $^1$H-NMR ($CD_3SOCD_3$, 400 MHz) δ1.00 [6H, s, C(CH$_3$)$_2$], 1.42 and 1.56 [2H+2H, 2m, CH$_2$C H$_2$C(CH$_3$)$_2$], 1.68 [3H, s, CH$_3$C=CC(CH$_3$)$_2$], 1.87 (2H, m, SCH$_2$CH$_2$), 1.93 and 1.94 [3H+3H, 2s, CH$_3$C=(CH)$_3$C(C H$_3$)=CHCO], 1.99 (2H, m, CH$_2$C=), 2.14 (2H, m, SCH$_2$), 3.95 (1H, m, NCH), 5.83 (1H, s, =CHCO), 6.18 [3H, m, C H=CHC(CH$_3$)=CHCH=CH], 6.81 [1H, dd, J 15.4, 11.4 Hz, CH=CHC(CH$_3$)=CHCH=CH], 7.42 (1H, d, J7.3 Hz, NH), 7.93 [1H, d, J 15.4 Hz, CH=CHC(CH$_3$)=CHCH=C H].

Example 17

Synthesis of N-(all-trans-retinoyl)-L-cysteinesulfinic Acid (Sodium Salt) (V)

This compound was synthesized as described above for I, using 150 mg (0.5 mmol) of all-trans-retinoic acid and 77 mg (0.5 mmol) of L-cysteinesulfinic acid.

Yield: 28%.

$R_f$ 0.30–0.35. $^1$H-NMR ($CD_3SOCD_3$, 400 MHz) δ1.00 [6H, s, C(CH$_3$)$_2$], 1.43 and 1.56 [2H+2H, 2m, CH$_2$C H$_2$C(CH$_3$)$_2$], 1.67 [3H, s, CH$_3$C=CC(CH$_3$)$_2$], 1.96 [3H, s, CH$_3$C=(CH)$_3$C(CH$_3$)=CHCO], 2.00 (2H, m, CH$_2$C=), 2.26 (3H, S, CH$_3$C=CHCO), 2.88–3.00 (2H, m, SCH$_2$), 4.51 (1H, m, NCH), 5.84 (1H, s, =CHCO), 6.11–6.36 [4H, m, CH=CHC(CH$_3$)=CHCH=CH], 6.94 [1H, dd, J 15.0, 11.4 Hz, CH=CHC(CH$_3$)=CHCH=CH], 8.47 (1H, d, J 7.9 Hz, NH), ~12.6 (1H, br s, CO$_2$H).

Example 18

Synthesis of N-(13-cis-retinoyl)-L-cysteinesulfinic Acid (Sodium Salt) (VI)

This compound was synthesized as described above for I, using 150 mg (0.5 mmol) of 13-cis-retinoic acid and 77 mg (0.5 mmol) of L-cysteinesulfinic acid.

Yield: 23%.

$R_f$ 0.30–0.35, $^1$H-NMR ($CD_3SOCD_3$, 400 MHz) δ1.00 [6H, s, C(CH$_3$)$_2$], 1.42 and 1.56 [2H+2H, 2m, CH$_2$C $\underline{H}_2C(CH_3)_2$], 1.67 [3H, s, $C\underline{H}_3C=CC(CH_3)_2$], 1.95 and 1.97 [3H+3H, 2s, $C\underline{H}_3C=(CH)_3C(C\underline{H}_3)=CHCO$], 1.99 (2H, m, $C\underline{H}_2C=$), 2.51 (1H, dd, J 13.2, 2.9 Hz, $SC\underline{H}^aH^b$), 2.65 (1H, dd, J 13.2, 8.2 Hz, $SCH^a\underline{H}^b$), 4.77 (1H, m, $NC\underline{H}$), 5.72 (1H, s, =$C\underline{H}CO$), 6.20 [3H, m, $C\underline{H}=C\underline{H}C(CH_3)=C\underline{H}CH=CH$], 6.87 [1H, dd, J 15.6, 11.5 Hz, $CH=CHC(CH_3)=CHC\underline{H}=CH$], 7.88 [1H, d, J 15.6 Hz, $CH=CHC(CH_3)=CHCH=C\underline{H}$], 8.21 (1H, d, J 7.9 Hz, $N\underline{H}$).

Example 19

Evaluation of Cytotoxicity of Compound I in Cultures of Human Breast Adenocarcinoma MDA-MB-231 Cell Line, Related to Final Concentration of Compound I in Cultures The sodium salt of compound I was dissolved in saline (1 mg/ml). From this solution the working solutions of compound I in MEM with 5% FBS were prepared in different concentrations for adding to cultures, by means of consecutive dilutions.

Cultures of MDA-MB-231 cells were treated with drug solutions in MEM, containing 5% FBS, after sowing on day 1. Aliquots of working solutions (2 µL) with different concentrations of compound I were added to 200 µL cultures to a final concentration of compound I from $10^{-11}$ to $10^{-6}$ mol/L in the cultures. In control cultures, 2 µL of medium with 5% FBS was added as solvent control. After cultivation for two consecutive days, the number of living cells in the cultures was counted and the extent of growth inhibition of MDA-MB-231 cells calculated for evaluating the cytotoxicity of the tested solutions of compound 1.

After three days of cultivation the control cultures contained $(58.7\pm2.24)\times10^3$ cells.

Cultures treated with solutions of compound I had the following number of living cells:

| | | |
|---|---|---|
| $10^{-11}$ mol/L: | $(41.9 \pm 2.17) \times 10^3$, cell growth inhibition 28.6% | (p < 0.001); |
| $10^{-10}$ mol/L: | $(37.3 \pm 2.84) \times 10^3$, cell growth inhibition 36.5% | (p < 0.001); |
| $10^{-9}$ mol/L: | $(35.4 \pm 2.23) \times 10^3$, cell growth inhibition 39.7% | (p < 0.001); |
| $10^{-8}$ mol/L: | $(31.6 \pm 1.69) \times 10^3$, cell growth inhibition 46.2% | (p < 0.001); |
| $4 \times 10^{-8}$ mol/L: | $(31.2 \pm 1.72) \times 10^3$, cell growth inhibition 46.8% | (p < 0.001); |
| $10^{-7}$ mol/L: | $(30.5 \pm 0.89) \times 10^3$, cell growth inhibition 48.0% | (p < 0.001); |
| $10^{-6}$ mol/L: | $(29.5 \pm 1.36) \times 10^3$, cell growth inhibition 49.7% | (p < 0.001). |

It is thus shown, that compound I exerts a significant cytotoxic action against human breast adenocarcinoma cells. The extent of cell growth inhibition increased to 49.7% (p<0.001) by increasing the concentration of compound I.

Example 20

Evaluation of the Cytotoxicity of the Formulation Paclitaxel/compound I in Cultures of Human Breast Adenocarcinoma MDA-MB-231 Cell Line, Related to the Molar Ratio Paclitaxel Compound I The sodium salt of compound I was converted into the acidic form of compound I and dissolved in methanol. A solution of paclitaxel in methanol and a solution of compound I in methanol was mixed together. After stirring the organic solvent was evaporated. The resulting dried film was dissolved in saline.

Initial solutions of the formulation in saline at the molar ratios paclitaxel:compound I equal to 1:3, 1:4, 1:5, 1:6, 1:7 and 1:10 were prepared. From these solutions the working solutions in MEM with 5% FBS were prepared for adding to cultures. The concentration of paclitaxel was equal to $10^{-6}$ M.

Cultures of MDA-MB-231 cells were treated with drug solutions in MEM, containing 5% FBS, after sowing on day 1. Aliquots of the working solutions (2 µL) were added to 200 µL cultures to a final concentration of paclitaxel in the cultures equal to $10^{-8}$ M. In control cultures 2 µL of medium with 5% FBS was added as solvent control. After cultivation for two consecutive days, the number of living cells in cultures was calculated for evaluating the cytotoxicity of the tested solutions of the formulation.

After three days of cultivation the control cultures contained $(54.4\pm2.51)\times10^3$ cells.

Cultures, treated with paclitaxel in concentration of 10 nM, contained $(29.3\pm1.13)\times10^3$ cells, cell growth inhibition was 46.1% (p<0.001).

Cultures, treated with solutions of the formulation at a molar ratio of paclitaxel:compound I equal to 1:3, 1:4, 1:5, 1:6, 1:7 and 1:10 in medium with 5% FBS, had the following number of living cells:

1:3: $(20.1\pm1.53)\times10^3$, the cell growth inhibition being 63.1% (p<0.001), and the cell growth inhibition compared to that of paclitaxel was increased by 31.4% (p<0.002);

1:4: $(18.9\pm0.92)\times10^3$, the cell growth inhibition being 65.3% (p<0.001), and the cell growth inhibition compared to that of paclitaxel was increased by 35.5% (p<0.001);

1:5: $(17.4\pm1.18)\times10^3$, the cell growth inhibition being 68.0% (p<0.001), and the cell growth inhibition compared to that of paclitaxel was increased by 40.6% (p<0.001);

1:6: $(16.9\pm1.08)\times10^3$, the cell growth inhibition being 68.9% (p<0.001), and the cell growth inhibition compared to that of paclitaxel was increased by 42.3% (p<0.001);

1:7: $(15.8\pm1.34)\times10^3$, the cell growth inhibition being 71.0% (p<0.001), and the cell growth inhibition compared to that of paclitaxel was increased by 46.1% (p<0.001);

1:10: $(15.2\pm0.72)\times10^3$, the cell growth inhibition being 72.1% (p<0.001), and the cell growth inhibition compared to that of paclitaxel was increased by 48.1% (p<0.001).

Example 21

Comparative Cytotoxity Testing of Taxol® and an Inventive Formulation (Taxol®+Compound I) in Cultures of Human Breast Adenocarcinoma MDA-MB-231 Cell Line Related to Molar Ratios Paclitaxel:Compound I The sodium salt of compound I was converted into the acidic form of compound I and dissolved in methanol. The organic solvent was evaporated. The resulting dried film was dissolved in Taxol®.

Initial solutions of the inventive formulation at the molar ratios of paclitaxel to compound I equal to 1:1, 1:3, 1:6, 1:10, 1:15 and 1:20 were prepared. From these solutions the working solutions in MEM with 5% FBS were prepared for adding to the cultures. The concentration of paclitaxel was equal to $10^{-6}$ M.

Cultures of MDA-MB-231 cells were treated with drug solutions in MEM, containing 5% FBS, after sowing on day 1. Aliquots of the working solutions (2 µL) were added to 200 µL cultures to a final concentration of paclitaxel in the cultures equal to $10^{-8}$ M. In control cultures 2 μL of medium with 5% FBS was added as solvent control. After cultivation for two consecutive days the number of living cells in cultures was calculated for evaluating the cytotoxicity of tested solutions.

After three days of cultivation, the control cultures contained $(54.0\pm1.60)\times10^3$ cells.

Cultures, treated with Taxol® in concentration of 10 nM paclitaxel, contained $(29.0\pm0.91)\times10^3$ cells, the cell growth inhibition being 46.3% (p<0.001).

Cultures, treated with solutions of the inventive formulation (Taxol®+compound I) at the molar ratio paclitaxel: compound I equal to 1:1, 1:3, 1:6, 1:10, 1:15 and 1:20 in medium with 5% FBS, had the following number of living cells:
1:1: $(21.5\pm2.18)\times10^3$, the cell growth inhibition being 60.2% (p<0.001), and the cell growth inhibition compared to that of Taxol® was increased by 25.9% (p<0.01);
1:3: $(18.5\pm1.08)\times10^3$, the cell growth inhibition being 65.7% (p<0.001), and the cell growth inhibition compared to that of Taxol® was increased by 36.2% (p<0.001);
1:6: $(14.2\pm0.75)\times10^3$, the cell growth inhibition being 73.7% (p<0.001), and the cell growth inhibition compared to that of Taxol® was increased by 51.0% (p<0.001);
1:10: $(13.8\pm0.63)\times10^3$, the cell growth inhibition being 74.4% (p<0.001), and the cell growth inhibition compared to that of Taxol® was increased by 52.4% (p<0.001);
1:15: $(13.4\pm1.22)\times10^3$, the cell growth inhibition being 75.2% (p<0.001), and the cell growth inhibition compared to that of Taxol® was increased by 53.8% (p<0.001);
1:20: $(13.5\pm1.14)\times10^3$, cell growth inhibition being 75.0% (p<0.001), and the cell growth inhibition compared to that of Taxol® was increased by 53.4% (p<0.001).

Example 22

Evalution of the Cytotoxicity of Compound II in Cultures of Human Breast Adenocarcinoma MDA-MB-231 Cell Line Related to the Final Concentration of Compound II in Cultures The sodium salt of compound II was dissolved in saline (1 mg/ml). From this solution, the working solutions of compound II in MEM with 5% FBS in different concentrations were prepared by means of consecutive dilutions for adding to the cultures. Cultures of MDA-MB-231 cells were treated with drug solutions in MEM, containing 5% FBS, after sowing on day 1. Aliquots of working solutions (2 μL) with different concentrations of compound II were added to 200 μL cultures to a final concentration of compound II from $10^{-11}$ to $10^{-6}$ mol/L in the cultures. In the control cultures, 2 μL of medium with 5% FBS was added as solvent control. After cultivation for two consecutive days, the number of living cells in the cultures was counted and the extent of growth inhibition of MDA-MB-231 cells calculated for evaluating the cytotoxicity of the tested solutions of compound II.

After three days of cultivation the control cultures contained $(58.7\pm2.24)\times10^3$ cells.

Cultures, treated with solutions of compound II had the following number of living cells:

| $10^{-11}$ mol/L: | $(42.3 \pm 2.32) \times 10^3$, cell growth inhibition 27.9% (p < 0.001); |
|---|---|
| $10^{-10}$ mol/L: | $(38.1 \pm 1.18) \times 10^3$, cell growth inhibition 35.1% (p < 0.001); |
| $10^{-9}$ mol/L: | $(34.5 \pm 1.94) \times 10^3$, cell growth inhibition 41.2% (p < 0.001); |
| $10^{-8}$ mol/L: | $(31.4 \pm 1.62) \times 10^3$, cell growth inhibition 46.5% (p < 0.001); |
| $4 \times 10^{-8}$ mol/L: | $(31.2 \pm 2.33) \times 10^3$, cell growth inhibition 46.8% (p < 0.001); |
| $10^{-7}$ mol/L: | $(31.7 \pm 1.54) \times 10^3$, cell growth inhibition 46.0% (p < 0.001); |
| $10^{-6}$ mol/L: | $(28.4 \pm 1.02) \times 10^3$, cell growth inhibition 51.6% (p < 0.001). |

It is thus shown, that compound II exerts a significant cytotoxic action against human breast adenocarcinoma cells. The extent of cell growth inhibition increased to 51.6% (p<0.001) when the concentration of compound II was increased.

Example 23

Evaluation of the Cytotoxicity of the Formulation Paclitaxel/compound II in Cultures of Human Breast Adenocarcinoma MDA-MB-231 Cell Line in Relation to the Molar Ratio Paclitaxel:compound II Sodium salt of compound II was converted into the acidic form of compound II and dissolved in methanol. A solution of paclitaxel in methanol and a solution of compound II in methanol was mixed. After stirring, the organic solvent was evaporated. The resulting dried film was dissolved in saline.

Initial solutions of the formulation in saline at the molar ratios paclitaxel:compound II equal to 1:3, 1:4, 1:5, 1:6, 1:7 and 1:10 were prepared. From these solutions the working solutions in MEM with 5% FBS were prepared for adding to cultures. The concentration of paclitaxel was equal to $10^{-6}$ M.

Cultures of MDA-MB-231 cells were treated with drug solutions in MEM, containing 5% FBS, after sowing on day 1. Aliquots of the working solutions (2 μL) were added to 200 μL cultures to a final concentration of paclitaxel in the cultures equal to $10^{-8}$ M. In the control cultures 2 μL of medium with 5% FBS was added as solvent control. After cultivation for two consecutive days, the number of living cells in the cultures was calculated and the cytotoxicity of the tested solutions of the formulation was evaluated.

After three days of cultivation the control cultures contained $(54.4\pm2.51)\times10^3$ cells.

Cultures, treated with paclitaxel in a concentration of 10 nM, contained $(29.3\pm1.13)\times10^3$ cells, thus the cell growth inhibition was 46.1% (p<0.001).

Cultures, treated with solutions of the formulation at the molar ratios paclitaxel: compound II equal to 1:3, 1:4, 1:5, 1:6, 1:7 and 1:10 in medium with 5% FBS, had the following number of living cells:
1:3: $(20.9\pm1.52)\times10^3$, the cell growth inhibition being 61.6% (p<0.002), and the cell growth inhibition compared to that of paclitaxel was increased by 28.7% (p<0.01);
1:4: $(18.6\pm1.27)\times10^3$, the cell growth inhibition being 65.8% (p<0.001), and the cell growth inhibition compared to that of paclitaxel was increased by 36.5% (p<0.001);
1:5: $(17.3\pm1.16)\times10^3$, the cell growth inhibition being 68.2% (p<0.001), and the cell growth inhibition compared to that of paclitaxel was increased by 41.0% (p<0.001);
1:6: $(16.8\pm0.75)\times10^3$, the cell growth inhibition being 69.1% (p<0.001), and the cell growth inhibition compared to that of paclitaxel was increased by 42.7% (p<0.001);

1:7: $(16.3\pm1.20)\times10^3$, the cell growth inhibition being 70.0% (p<0.001), and the cell growth inhibition compared to that of paclitaxel was increased by 44.4% (p<0.001);

1:10: $(15.9\pm0.86)\times10^3$, the cell growth inhibition being 70.8% (p<0.001), and the cell growth inhibition compared to that of paclitaxel was increased by 45.7% (p<0.001).

Example 24

Comparative Cytotoxity Testing of Taxol® and the Inventive Formulation (Taxol®+compound II) in Cultures of Human Breast Adenocarcinoma MDA-MB-231 Cell Line, in Relation to the Molar Ratio of Paclitaxel:compound II The sodium salt of compound II was converted into the acidic form of compound II and dissolved in methanol. The organic solvent was evaporated. The resulting dried film was dissolved in Taxol®.

Initial solutions of the inventive formulation at the molar ratios paclitaxel:compound II equal to 1:1, 1:3, 1:6, 1:10, 1:15 and 1:20 were prepared. From these solutions the working solutions in MEM with 5% FBS for adding to cultures were prepared. The concentration of paclitaxel was equal to $10^{-6}$ M.

Cultures of MDA-MB-231 cells were treated with drug solutions in MEM, containing 5% FBS, after sowing on day 1. Aliquots of the working solutions (2 μL) were added to 200 μL cultures to final concentration of paclitaxel in cultures equal to $10^{-8}$ M. In control cultures 2 μL of medium with 5% FBS was added as solvent control. After cultivation for two consecutive days the number of living cells in the cultures was calculated and the cytotoxicity of tested solutions evaluated.

After three days of cultivation the control cultures contained $(54.0\pm1.60)\times10^3$ cells.

Cultures, treated with Taxol® in a concentration corresponding to 10 nM paclitaxel, contained $(29.0\pm0.91)\times10^3$ cells, thus the cell growth inhibition was 46.3% (p<0.001);

Cultures, treated with solutions of the inventive formulation (Taxol®+compound II) at the molar ratios paclitaxel:compound II equal to 1:1, 1:3, 1:6, 1:10, 1:15 and 1:20 in medium with 5% FBS, had the following number of living cells:

1:1: $(21.1\pm1.76)\times10^3$, the cell growth inhibition being 60.9% (p<0.001), and the cell growth inhibition compared to that of Taxol® was increased by 27.2% (p<0.01);

1:3: $(19.8\pm1.81)\times10^3$, the cell growth inhibition being 63.3% (p<0.001), and the cell growth inhibition compared to that of Taxol® was increased by 31.7% (p<0.001);

1:6: $(14.7\pm1.46)\times10^3$, the cell growth inhibition being 72.8% (p<0.001), and the cell * growth inhibition compared to that of Taxol® was increased by 49.3% (p<0.001);

1:10: $(14.2\pm1.15)\times10^3$, the cell growth inhibition being 73.7% (p<0.001), and the cell growth inhibition compared to that of Taxol® was increased by 51.0% (p<0.001);

1:15: $(13.9\pm1.02)\times10^3$, the cell growth inhibition being 74.3% (p<0.001), and the cell growth inhibition compared to that of Taxol® was increased by 52.1% (p<0.001);

1:20: $(13.3\pm1.27)\times10^3$, the cell growth inhibition being 75.4% (p<0.001), and the cell growth inhibition compared to that of Taxol® was increased by 54.1% (p<0.001).

Example 25

Evaluation of the Cytotoxicity of Compound III in Cultures of Human Breast Adenocarcinoma MDA-MB-231 Cell Line, Related to the Final Concentration of Compound III in the Cultures The sodium salt of compound III was dissolved in saline (1 mg/ml). From this solution the working solutions of compound III in MEM with 5% FBS in different concentrations were prepared by means of consecutive dilutions for adding to cultures.

Cultures of MDA-MB-231 cells were treated with drug solutions in MEM, containing 5% FBS, after sowing on day 1. Aliquots of working solutions (2 μL) with different concentrations of compound III were added to 200 μL cultures to final concentrations of compound III from $10^{-11}$ to $10^{-6}$ mol/L in cultures. In the control cultures 2 μL of medium with 5% FBS were added as solvent control. After cultivation for two consecutive days, the number of living cells in cultures was counted and extent of growth inhibition of MDA-MB-231 cells was calculated for evaluating the cytotoxicity of tested solutions of compound III.

After three days of cultivation the control cultures contained $(54.3\pm2.12)\times10^3$ cells.

Cultures, treated with solutions of compound III had the following number of living cells:

| | |
|---|---|
| $10^{-11}$ mol/L: | $(45.1 \pm 3.51) \times 10^3$, cell growth inhibition 16.9% (p < 0.05); |
| $10^{-10}$ mol/L: | $(45.9 \pm 2.84) \times 10^3$, cell growth inhibition 15.5% (p < 0.05); |
| $10^{-9}$ mol/L: | $(43.6 \pm 2.57) \times 10^3$, cell growth inhibition 19.7% (p < 0.01); |
| $10^{-8}$ mol/L: | $(40.3 \pm 3.36) \times 10^3$, cell growth inhibition 25.8% (p < 0.01); |
| $4 \times 10^{-8}$ mol/L: | $(36.5 \pm 2.08) \times 10^3$, cell growth inhibition 32.8% (p < 0.001); |
| $10^{-7}$ mol/L: | $(35.6 \pm 1.68) \times 10^3$, cell growth inhibition 34.4% (p < 0.001); |
| $10^{-6}$ mol/L: | $(34.7 \pm 1.52) \times 10^3$, cell growth inhibition 36.1% (p < 0.001). |

It is thus shown, that compound III alone exerts a significant cytotoxic action against human breast adenocarcinoma cells. The extent of cell growth inhibition was increased to 36.1% (p<0.001) by increasing the concentration of compound III.

Example 26

Evaluation of the Cytotoxicity of the Formulation Paclitaxel/compound III in Cultures of Human Breast Adenocarcinoma MDA-MB-231 Cell Line, Related to the Molar Ratio Paclitaxel:compound III The sodium salt of compound III was converted into the acidic form of compound III and dissolved in methanol. A solution of paclitaxel in methanol and solution of compound III in methanol was mixed. After stirring the organic solvent was evaporated. The resulting dried film was dissolved in saline.

Initial solutions of the formulation in saline at the molar ratios paclitaxel:compound III equal to 1:3, 1:4, 1:5, 1:6, 1:7 and 1:10 were prepared. From these solutions the working solutions in MEM with 5% FBS for adding to cultures were prepared. The concentration of paclitaxel was equal to $10^{-6}$ M.

Cultures of MDA-MB-231 cells were treated with drug solutions in MEM, containing 5% FBS, after sowing on day 1. Aliquots of the working solutions (2 μL) were added to 200 μL cultures to a final concentration of paclitaxel in cultures equal to $10^{-8}$ M. In the control cultures 2 μL of medium with 5% FBS was added as solvent control. After cultivation for two consecutive days the number of living cells in the cultures was calculated, and the cytotoxicity of the tested solutions of the formulation evaluated.

After three days of cultivation the control cultures contained $(53.7\pm1.96)\times10^3$ cells.

Cultures, treated with paclitaxel in concentration of 10 nM, contained $(31.8\pm1.85)\times10^3$ cells, the cell growth inhibition thus being 40.8% (p<0.001). Cultures, treated with solutions of the formulation at the molar ratios paclitaxel: compound III equal to 1:3, 1:4, 1:5, 1:6, 1:7 and 1:10 in medium with 5% FBS, had the following number of living cells:

1:3: $(24.7\pm2.17)\times10^3$, the cell growth inhibition being 54.0% (p<0.001), and the cell growth inhibition compared to that of paclitaxel was increased by 22.3% (p<0.05);
1:4: $(24.0\pm2.23)\times10^3$, the cell growth inhibition being 55.3% (p<0.001), and the cell growth inhibition compared to that of paclitaxel was increased by 24.5% (p<0.05);
1:5: $(22.5\pm1.91)\times10^3$, the cell growth inhibition being 58.1% (p<0.001), and the cell growth inhibition compared to that of paclitaxel was increased by 29.2% (p<0.01);
1:6: $(22.3\pm1.88)\times10^3$, the cell growth inhibition being 58.5% (p<0.001), and the cell growth inhibition compared to that of paclitaxel was increased by 29.9% (p<0.01);
1:7: $(21.9\pm1.90)\times10^3$, the cell growth inhibition being 59.2% (p<0.001), and the cell growth inhibition compared to that of paclitaxel was increased by 31.1% (p<0.01);
1:10: $(21.7\pm1.56)\times10^3$, the cell growth inhibition being 59.6% (p<0.001), and the cell growth inhibition compared to that of paclitaxel was increased by 31.8% (p<0.002).

Example 27

Comparative Cytotoxity Testing of Taxol® and an Inventive Formulation (Taxol®+Compound III) in Cultures of Human Breast Adenocarcinoma MDA-MB-231 Cell Line Related to the Molar Ratio Paclitaxel:compound III The sodium salt of compound III was converted into the acidic form of compound III and dissolved in methanol. The organic solvent was evaporated. The resulting dried film was dissolved in Taxol®.

Initial solutions of the inventive formulation were prepared having the molar ratio of paclitaxel to compound III equal to 1:1, 1:3, 1:6, 1:10, 1:15 and 1:20. From these solutions, the working solutions in MEM with 5% FBS were prepared for adding to cultures. The concentration of paclitaxel was equal to $10^{-6}$ M.

Cultures of MDA-MB-231 cells were treated with drug solutions in MEM, containing 5% FBS, after sowing on day 1. Aliquots of the working solutions (2 µL) were added to 200 µL cultures to final concentration of paclitaxel in cultures equal to $10^{-8}$ M. In control cultures 2 µL of medium with 5% FBS was added as solvent control. After cultivation for two consecutive days the number of living cells in the cultures was calculated, and the cytotoxicity of the tested solutions evaluated.

After three days of cultivation, the control cultures contained $(55.8\pm1.78)\times10^3$ cells.

Cultures, treated with Taxol® in concentration of 10 nM paclitaxel, contained $(31.4\pm1.61)\times10^3$ cells, the cell growth inhibition thus being 43.7% (p<0.001).

Cultures, treated with solutions of the inventive formulation (Taxol®+compound III) at the molar ratios paclitaxel: compound III equal to 1:1, 1:3, 1:6, 1:10, 1:15 and 1:20 in medium with 5% FBS, had the following number of living cells:

1:1: $(27.4\pm1.56)\times10^3$, the cell growth inhibition being 50.9% (p<0.001), and the cell growth inhibition compared to that of Taxol® was increased by 12.7% (p>0.05);
1:3: $(23.7\pm1.42)\times10^3$, the cell growth inhibition being 57.5% (p<0.001), and the cell growth inhibition compared to that of Taxol® was increased by 24.5% (p<0.01);
1:6: $(20.5\pm1.17)\times10^3$, the cell growth inhibition being 63.3% (p<0.001), and the cell growth inhibition compared to that of Taxol® was increased by 34.7% (p<0.001);
1:10: $(19.6\pm1.23)\times10^3$, the cell growth inhibition being 64.9% (p<0.001), and the cell growth inhibition compared to that of Taxol® was increased by 37.6% (p<0.001);
1:15: $(19.8\pm1.64)\times10^3$, the cell growth inhibition being 64.5% (p<0.001), and the cell growth inhibition compared to that of Taxol® was increased by 36.9% (p<0.001);
1:20: $(19.5\pm1.49)\times10^3$, the cell growth inhibition being 65.1% (p<0.001), and the cell growth inhibition compared to that of Taxol® was increased by 37.9% (p<0.001).

Example 28

Evalution of the Cytotoxicity of Compound IV in Cultures of Human Breast Adenocarcinoma MDA-MB-231 Cell Line in Relation to the Final Concentration of Compound IV in Cultures The sodium salt of compound IV was dissolved in saline (1 mg/ml). From this solution, the working solutions of compound IV in MEM with 5% FBS in different concentrations were prepared by means of consecutive dilutions for adding to the cultures.

Cultures of MDA-MB-231 cells were treated with drug solutions in MEM, containing 5% FBS, after sowing on day 1. Aliquots of working solutions (2 µL) with different concentrations of compound IV were added to 200 µL cultures to a final concentration of compound IV ranging from $10^{-11}$ to $10^{-6}$ mol/L in the cultures. In control cultures 2 µL of medium with 5% FBS was added as solvent control. After cultivation for two consecutive days, the number of living cells in cultures was counted and the extent of growth inhibition of MDA-MB-231 cells calculated for evaluation of the cytotoxicity of tested solutions of compound IV.

After three days of cultivation the control cultures contained $(52.7\pm1.85)\times10^3$ cells.

Cultures, treated with solutions of compound IV had the following number of living cells:

| | |
|---|---|
| $10^{-11}$ mol/L: | $(44.9 \pm 3.02) \times 10^3$, cell growth inhibition 14.8% ($p < 0.05$); |
| $10^{-10}$ mol/L: | $(44.2 \pm 3.35) \times 10^3$, cell growth inhibition 16.1% ($p < 0.05$); |
| $10^{-9}$ mol/L: | $(43.6 \pm 3.21) \times 10^3$, cell growth inhibition 17.3% ($p < 0.05$); |
| $10^{-8}$ mol/L: | $(39.6 \pm 2.74) \times 10^3$, cell growth inhibition 24.9% ($p < 0.01$); |
| $4 \times 10^{-8}$ mol/L: | $(37.1 \pm 2.56) \times 10^3$, cell growth inhibition 29.6% ($p < 0.001$); |
| $10^{-7}$ mol/L: | $(36.3 \pm 2.08) \times 10^3$, cell growth inhibition 31.1% ($p < 0.001$); |
| $10^{-6}$ mol/L: | $(35.9 \pm 2.29) \times 10^3$, cell growth inhibition 31.9% ($p < 0.001$). |

It is thus shown, that compound IV exerts a significant cytotoxic action against human breast adenocarcinoma cells. By increasing the concentration of compound IV, it was possible to increase the extent of cell growth inhibition to 31.9% (p<0.001).

Example 29

Evaluation of the Cytotoxicity of the Formulation Paclitaxel/compound IV in Cultures of Human Breast Adenocarcinoma MDA-MB-231 Cell Line in Relation to the Molar Ratio Paclitaxel:compound IV The sodium salt of compound IV was converted into the acidic form of compound IV and dissolved in methanol. A solution of paclitaxel in methanol and a solution of compound IV in methanol was mixed. After stirring, the organic solvent was evaporated. The resulting dried film was dissolved in saline.

Initial solutions of the formulation in saline at the molar ratios paclitaxel:compound IV equal to 1:3, 1:4, 1:5, 1:6, 1:7 and 1:10 were prepared. From these solutions the working solutions in MEM with 5% FBS were prepared for adding to the cultures. The concentration of paclitaxel was equal to $10^{-6}$ M.

Cultures of MDA-MB-231 cells were treated with drug solutions in MEM, containing 5% FBS, after sowing on day 1. Aliquots of the working solutions (2 µL) were added to 200 µL cultures to final concentration of paclitaxel in cultures equal to $10^{-8}$ M. In control cultures 2 µL of medium with 5% FBS were added as solvent control. After cultivation for two consecutive days the number of living cells in cultures was calculated for evaluating the cytotoxicity of tested solutions of the formulation.

After three days of cultivation the control cultures contained $(55.1\pm2.38)\times10^3$ cells.

Cultures, treated with paclitaxel in concentration of 10 nM, contained $(30.7\pm2.15)\times10^3$ cells, the cell growth inhibition thus being 44.3% ($p<0.001$).

Cultures, treated with solutions of the formulation at the molar ratios paclitaxel:compound IV equal to 1:3, 1:4, 1:5, 1:6, 1:7 and 1:10 in medium with 5% FBS, had the following number of living cells:

1:3: $(24.3\pm1.74)\times10^3$, the cell growth inhibition was 55.9% ($p<0.001$), and the cell growth inhibition compared to that of paclitaxel was increased by 20.8% ($p<0.05$);
1:4: $(23.7\pm2.03)\times10^3$, the cell growth inhibition was 57.0% ($p<0.001$), and the cell growth inhibition compared to that of paclitaxel was increased by 22.8% ($p<0.05$);
1:5: $(22.1\pm1.52)\times10^3$, the cell growth inhibition was 59.9% ($p<0.001$), and the cell growth inhibition compared to that of paclitaxel was increased by 28.0% ($p<0.01$);
1:6: $(21.9\pm1.16)\times10^3$, the cell growth inhibition was 60.3% ($p<0.001$), and the cell growth inhibition compared to that of paclitaxel was increased by 28.7% ($p<0.01$);
1:7: $(21.8\pm1.98)\times10^3$, the cell growth inhibition was 60.4% ($p<0.001$), and the cell growth inhibition compared to that of paclitaxel was increased by 29.0% ($p<0.02$);
1:10: $(21.6\pm1.45)\times10^3$, the cell growth inhibition was 60.8% ($p<0.001$), and the cell growth inhibition compared to that of paclitaxel was increased by 29.6% ($p<0.01$).

Example 30

Comparative Cytotoxity Testing of Taxol® and the Inventive Formulation (Taxol®+compound IV) in Cultures of Human Breast Adenocarcinoma MDA-MB-231 Cell Line in Relation to the Molar Ratio Paclitaxel:compound IV The sodium salt of compound IV was converted into the acidic form of compound IV and dissolved in methanol. The organic solvent was evaporated. The resulting dried film was dissolved in Taxol®. initial solutions of inventive formulation at the molar ratios paclitaxel: compound IV equal to 1:1, 1:3, 1:6, 1:10, 1:15 and 1:20 were prepared. From these solutions the working solutions in MEM with 5% FBS for adding to cultures were prepared. The concentration of paclitaxel was equal to $10^{-6}$ M.

Cultures of MDA-MB-231 cells were treated with drug solutions in MEM, containing 5% FBS, after sowing on day 1. Aliquots of the working solutions (2 µL) were added to 200 µL cultures to final concentration of paclitaxel in cultures equal to $10^{-8}$ M. In control cultures 2 µL of medium with 5% FBS were added as solvent control. After cultivation for two consecutive days the number of living cells in cultures was calculated for evaluating the cytotoxicity of tested solutions.

After three days of cultivation the control cultures contained $(50.4\pm2.45)\times10^3$ cells.

Cultures, treated with Taxol® in a concentration of 10 nM paclitaxel, contained $(29.5\pm1.32)\times10^3$ cells, cell growth inhibition was 41.5% ($p<0.001$);

Cultures, treated with solutions of the inventive formulation (Taxol®+compound IV) at the molar ratios paclitaxel:compound IV equal to 1:1, 1:3, 1:6, 1:10, 1:15 and 1:20 in medium with 5% FBS, had the following number of living cells:

1:1: $(26.2\pm1.15)\times10^3$, the cell growth inhibition was 48.0% ($p<0.001$), and the cell growth inhibition compared to that of Taxol® was increased by 11.2% ($p>0.05$);
1:3: $(23.3\pm1.68)\times10^3$, the cell growth inhibition was 53.8% ($p<0.001$), and the cell growth inhibition compared to that of Taxol® was increased by 21.0% ($p<0.02$);
1:6: $(19.8\pm1.26)\times10^3$, the cell growth inhibition was 60.7% ($p<0.001$), and the cell growth inhibition compared to that of Taxol® was increased by 32.9% ($p<0.001$);
1:10: $(19.1\pm1.04)\times10^3$, the cell growth inhibition was 62.1% ($p<0.001$), and the cell growth inhibition compared to that of Taxol® was increased by 35.3% ($p<0.001$);
1:15: $(18.9\pm1.73)\times10^3$, the cell growth inhibition was 62.5% ($p<0.001$), and the cell growth inhibition compared to that of Taxol® was increased by 35.9% ($p<0.001$);
1:20: $(19.3\pm1.42)\times10^3$, the cell growth inhibition was 61.7% ($p<0.001$), and the cell growth inhibition compared to that of Taxol® was increased by 34.6% ($p<0.001$).

Example 31

Evaluation of the Cytotoxicity of Compound V in Cultures of Human Breast Adenocarcinoma MDA-MB-231 Cell Line Related to the Final Concentration of Compound V in Cultures The sodium salt of compound V was dissolved in saline (1 mg/ml). From this solution the working solutions of compound V in MEM with 5% FBS in different concentrations were prepared by means of consecutive dilutions for adding to the cultures.

Cultures of MDA-MB-231 cells were treated with drug solutions in MEM, containing 5% FBS, after sowing on day 1. Aliquots of working solutions (2 µL) with different concentrations of compound V were added to 200 µL cultures to a final concentration of compound V from $10^{-11}$ to $10^{-6}$ mol/L in the cultures. In control cultures 2 µL of medium with 5% FBS were added as solvent control. After cultivation for two consecutive days, the number of living cells in cultures was counted and extent of growth inhibition of MDA-MB-231 cells was calculated for evaluating the cytotoxicity of tested solutions of compound V.

After three days of cultivation the control cultures contained $(54.3\pm2.12)\times10^3$ cells.

Cultures, treated with solutions of compound V had the following number of living cells:

| | |
|---|---|
| $10^{-11}$ mol/L: | $(47.1 \pm 2.41) \times 10^3$, cell growth inhibition 13.3% ($p < 0.05$); |
| $10^{-10}$ mol/L: | $(46.3 \pm 2.49) \times 10^3$, cell growth inhibition 14.7% ($p < 0.05$); |
| $10^{-9}$ mol/L: | $(45.5 \pm 2.80) \times 10^3$, cell growth inhibition 16.2% ($p < 0.05$); |
| $10^{-8}$ mol/L: | $(41.1 \pm 2.34) \times 10^3$, cell growth inhibition 24.3% ($p < 0.002$); |
| $4 \times 10^{-8}$ mol/L: | $(39.6 \pm 1.75) \times 10^3$, cell growth inhibition 27.1% ($p < 0.001$); |
| $10^{-7}$ mol/L: | $(39.3 \pm 1.22) \times 10^3$, cell growth inhibition 27.6% ($p < 0.001$); |
| $10^{-6}$ mol/L: | $(38.1 \pm 1.86) \times 10^3$, cell growth inhibition 29.8% ($p < 0.001$). |

It is thus shown, that compound V exerts a significant cytotoxic action against human breast adenocarcinoma cells. By increasing the concentration of compound V alone, it was possible to increase the extent of cell growth inhibition to 29.8% ($p < 0.001$).

Example 32

Evaluation of the Cytotoxicity of the Formulation Paclitaxel/compound V in Cultures of Human Breast Adenocarcinoma MDA-MB-231 Cell Line in Relation to the Molar Ratio Paclitaxel:compound V The sodium salt of compound V was converted into the acidic form of compound V and dissolved in methanol. A solution of paclitaxel in methanol and a solution of compound V in methanol was mixed. After stirring, the organic solvent was evaporated. The resulting dried film was dissolved in saline.

Initial solutions of the formulation in saline at the molar ratio paclitaxel:compound V equal to 1:3, 1:4, 1:5, 1:6, 1:7 and 1:10 were prepared. From these solutions the working solutions in MEM with 5% FBS were prepared for adding to the cultures. The concentration of paclitaxel was equal to $10^{-6}$ M.

Cultures of MDA-MB-231 cells were treated with drug solutions in MEM, containing 5% FBS, after sowing on day 1. Aliquots of the working solutions (2 $\mu$L) were added to 200 $\mu$L cultures to a final concentration of paclitaxel in the cultures equal to $10^{-8}$ M. In the control cultures 2 $\mu$L of medium with 5% FBS was added as solvent control. After cultivation for two consecutive days, the number of living cells in cultures was calculated, and the cytotoxicity of the tested solutions evaluated.

After three days of cultivation the control cultures contained $(53.7 \pm 1.96) \times 10^3$ cells.

Cultures, treated with paclitaxel in a concentration of 10 nM, contained $(31.8 \pm 1.85) \times 10^3$ cells, the cell growth inhibition being 40.8% ($p < 0.001$). Cultures, treated with solutions of the formulation at the molar ratio paclitaxel/compound V equal to 1:3, 1:4, 1:5, 1:6, 1:7 and 1:10 in medium with 5% FBS, had the following number of living cells:

1:3: $(26.1 \pm 2.33) \times 10^3$, the cell growth inhibition was 51.4% ($p < 0.001$), and the cell growth inhibition compared to that of paclitaxel was increased by 17.9% ($p > 0.05$);
1:4: $(25.7 \pm 2.14) \times 10^3$, the cell growth inhibition was 52.1% ($p < 0.001$), and the cell growth inhibition compared to that of paclitaxel was increased by 19.2% ($p > 0.05$);
1:5: $(24.3 \pm 2.06) \times 10^3$, the cell growth inhibition was 54.7% ($p < 0.001$), and the cell growth inhibition compared to that of paclitaxel was increased by 23.6% ($p < 0.05$);
1:6: $(24.1 \pm 1.87) \times 10^3$, the cell growth inhibition was 55.1% ($p < 0.001$), and the cell growth inhibition compared to that of paclitaxel was increased by 24.2% ($p < 0.02$);
1:7: $(23.9 \pm 2.08) \times 10^3$, the cell growth inhibition was 55.5% ($p < 0.001$), and the cell growth inhibition compared to that of paclitaxel was increased by 24.8% ($p < 0.02$);
1:10: $(23.7 \pm 1.65) \times 10^3$, the cell growth inhibition was 55.9% ($p < 0.001$), and the cell growth inhibition compared to that of paclitaxel was increased by 25.5% ($p < 0.01$).

Example 33

Comparative Cytotoxicity Testing of Taxol® and an Inventive Formulation (Taxol®+Compound V) in Cultures of Human Breast Adenocarcinoma MDA-MB-231 Cell Line Related to Molar Ratios Paclitaxel:compound V The sodium salt of compound V was converted into the acidic form of compound V and dissolved in methanol. The organic solvent was evaporated. The resulting dried film was dissolved in Taxol®.

Initial solutions of the inventive formulation at the molar ratios of paclitaxel to compound V equal to 1:1, 1:3, 1:6, 1:10, 1:15 and 1:20 were prepared. From these solutions the working solutions in MEM with 5% FBS were prepared for adding to the cultures. The concentration of paclitaxel was equal to $10^{-6}$ M.

Cultures of MDA-MB-231 cells were treated with drug solutions in MEM, containing 5% FBS, after sowing on day 1. Aliquots of the working solutions (2 $\mu$L) were added to 200 $\mu$L cultures to a final concentration of paclitaxel in cultures equal to $10^{-8}$ M. In control cultures 2 $\mu$L of medium with 5% FBS were added as solvent control. After cultivation for two consecutive days the number of living cells in cultures was calculated, and the cytotoxicity of the tested solutions evaluated.

After three days of cultivation, the control cultures contained $(55.8 \pm 1.78) \times 10^3$ cells.

Cultures, treated with Taxol® in a concentration of 10 nM paclitaxel, contained $(31.4 \pm 1.61) \times 10^3$ cells, the cell growth inhibition was 43.7% ($p < 0.001$).

Cultures, treated with solutions of the inventive formulation (Taxol®+compound V) at the molar ratio paclitaxel:compound V equal to 1:1, 1:3, 1:6, 1:10, 1:15 and 1:20 in medium with 5% FBS, had the following number of living cells:

1:1: $(28.1 \pm 2.14) \times 10^3$, the cell growth inhibition was 49.6% ($p < 0.001$), and the cell growth inhibition compared to that of Taxol® was increased by 10.5% ($p > 0.05$);
1:3: $(25.3 \pm 1.78) \times 10^3$, the cell growth inhibition was 54.7% ($p < 0.001$), and the cell growth inhibition compared to that of Taxol® was increased by 19.4% ($p < 0.05$);
1:6: $(22.8 \pm 1.85) \times 10^3$, the cell growth inhibition was 59.1% ($p < 0.001$), and the cell growth inhibition compared to that of Taxol® was increased by 27.4% ($p < 0.01$);
1:10: $(21.9 \pm 1.12) \times 10^3$, the cell growth inhibition was 60.8% ($p < 0.001$), and the cell growth inhibition compared to that of Taxol® was increased by 30.3% ($p < 0.001$);
1:15: $(21.8 \pm 1.33) \times 10^3$ the cell growth inhibition was 60.9% ($p < 0.001$), and the cell growth inhibition compared to that of Taxol® was increased by 30.6% ($p < 0.001$);
1:20: $(22.0 \pm 1.57) \times 10^3$, the cell growth inhibition was 60.6% ($p < 0.001$), and the cell growth inhibition compared to that of Taxol® was increased by 29.9% ($p < 0.002$).

Example 34

Evalution of the Cytotoxicity of Compound VI in Cultures of Human Breast Adenocarcinoma MDA-MB-231 Cell Line in Relation to the Final Concentration of Compound VI in the Cultures The sodium salt of compound VI was dissolved in saline (1 mg/ml). From this solution, the working solutions of compound VI in MEM with 5% FBS in different concentrations were prepared by means of consecutive dilutions for adding to the cultures.

Cultures of MDA-MB-231 cells were treated with drug solutions in MEM, containing 5% FBS, after sowing on day 1. Aliquots of the working solutions (2 µL) with different concentrations of compound VI were added to 200 µL cultures to a final concentration of compound VI ranging from $10^{-11}$ to $10^{-6}$ mol/L. In control cultures 2 µL of medium with 5% FBS was added as solvent control. After cultivation for two consecutive days, the number of living cells in cultures was counted, the extent of growth inhibition of MDA-MB-231 cells calculated, and the cytotoxicity of tested solutions of compound VI evaluated.

After three days of cultivation the control cultures contained $(52.7\pm1.85)\times10^3$ cells.

Cultures, treated with solutions of compound VI had the following number of living cells:

| | | |
|---|---|---|
| $10^{-11}$ mol/L: | $(46.2 \pm 3.54) \times 10^3$, cell growth inhibition 12.3% ($p < 0.05$); | |
| $10^{-10}$ mol/L: | $(45.5 \pm 2.68) \times 10^3$, cell growth inhibition 13.7% ($p < 0.05$); | |
| $10^{-9}$ mol/L: | $(45.3 \pm 2.55) \times 10^3$, cell growth inhibition 14.0% ($p < 0.05$); | |
| $10^{-8}$ mol/L: | $(40.9 \pm 2.88) \times 10^3$, cell growth inhibition 22.4% ($p < 0.01$); | |
| $4 \times 10^{-8}$ mol/L: | $(39.6 \pm 2.70) \times 10^3$, cell growth inhibition 24.9% ($p < 0.01$); | |
| $10^{-7}$ mol/L: | $(39.1 \pm 2.16) \times 10^3$, cell growth inhibition 25.8% ($p < 0.001$); | |
| $10^{-6}$ mol/L: | $(38.3 \pm 2.34) \times 10^3$, cell growth inhibition 27.3% ($p < 0.001$). | |

It is thus shown, that compound VI exerts a significant cytotoxic action against human breast adenocarcinoma cells. By increasing the concentration of compound VI, it was possible to increase the extent of cell growth inhibition to 27.3% ($p<0.001$).

Example 35

Evaluation of the Cytotoxicity of the Formulation Paclitaxel/compound VI in Cultures of Human Breast Adenocarcinoma MDA-MB-231 Cell Line in Relation to the Molar Ratio Paclitaxel:compound VI The sodium salt of compound VI was converted into the acidic form of compound VI and dissolved in methanol. A solution of paclitaxel in methanol and a solution of compound VI in methanol was mixed. After stirring, the organic solvent was evaporated. The resulting dried film was dissolved in saline.

Initial solutions of the formulation in saline at the molar ratio paclitaxel:compound VI equal to 1:3, 1:4, 1:5, 1:6, 1:7 and 1:10 were prepared. From these solutions the working solutions in MEM with 5% FBS were prepared for adding to cultures. The concentration of paclitaxel was equal to $10^{-6}$ M.

Cultures of MDA-MB-231 cells were treated with drug solutions in MEM, containing 5% FBS, after sowing on day 1. Aliquots of the working solutions (2 µL) were added to 200 µL cultures to final concentration of paclitaxel in cultures equal to $10^{-8}$ M. In the control cultures 2 µL of medium with 5% FBS was added as solvent control. After cultivation for two consecutive days, the number of living cells in the cultures was calculated and the cytotoxicity of tested solutions evaluated.

After three days of cultivation the control cultures contained $(55.1\pm2.38)\times10^3$ cells.

Cultures, treated with paclitaxel in a concentration of 10 nM, contained $(30.7\pm2.15)\times10^3$ cells, and the cell growth inhibition was 44.3% ($p<0.001$).

Cultures, treated with solutions of the formulation at the molar ratios paclitaxel:compound VI equal to 1:3, 1:4, 1:5, 1:6, 1:7 and 1:10 in medium with 5% FBS, had the following number of living cells:

1:3: $(25.6\pm2.42)\times10^3$, the cell growth inhibition was 53.5% ($p<0.001$), and the cell growth inhibition compared to that of paclitaxel was increased by 16.6% ($p>0.05$);

1:4: $(25.0\pm2.23)\times10^3$, the cell growth inhibition was 54.6% ($p<0.001$), and the cell growth inhibition compared to that of paclitaxel was increased by 18.6% ($p>0.05$);

1:5: $(24.0\pm1.84)\times10^3$, the cell growth inhibition was 56.4% ($p<0.001$), and the cell growth inhibition compared to that of paclitaxel was increased by 21.8% ($p<0.05$);

1:6: $(23.7\pm1.69)\times10^3$, the cell growth inhibition was 57.0% ($p<0.001$), and the cell growth inhibition compared to that of paclitaxel was increased by 22.8% ($p<0.05$);

1:7: $(23.4\pm1.36)\times10^3$, the cell growth inhibition was 57.5% ($p<0.001$), and the cell growth inhibition compared to that of paclitaxel was increased by 23.8% ($p<0.02$);

1:10: $(23.1\pm1.75)\times10^3$, the cell growth inhibition was 58.1% ($p<0.001$), and the cell growth inhibition compared to that of paclitaxel was increased by 24.8% ($p<0.02$).

Example 36

Comparative Cytotoxity Testing of Taxol® and the Inventive Formulation (Taxol®+Compound VI) in Cultures of Human Breast Adenocarcinoma MDA-MB-231 Cell Line, in Relation to the Molar Ratio Paclitaxel:compound VI The sodium salt of compound VI was converted into the acidic form of compound VI and dissolved in methanol. The organic solvent was evaporated. The resulting dried film was dissolved in Taxol®

Initial solutions of the inventive formulation at the molar ratio paclitaxel:compound VI equal to 1:1, 1:3, 1:6, 1:10, 1:15 and 1:20 were prepared. From these solutions the working solutions in MEM with 5% FBS were prepared for adding to cultures. The concentration of paclitaxel was equal to $10^{-6}$ M.

Cultures of MDA-MB-231 cells were treated with drug solutions in MEM, containing 5% FBS, after sowing on day 1. Aliquots of the working solutions (2 µL) were added to 200 µL cultures to a final concentration of paclitaxel in cultures equal to $10^{-8}$ M. In the control cultures 2 µL of medium with 5% FBS were added as solvent control. After cultivation for two consecutive days, the number of living cells in cultures was calculated, and the cytotoxicity of tested solutions evaluated.

After three days of cultivation the control cultures contained $(50.4\pm2.45)\times10^3$ cells.

The cultures, treated with Taxol® in concentration of 10 nM paclitaxel, contained $(29.5\pm1.32)\times10^3$ cells, cell growth inhibition was 41.5% ($p<0.001$);

The cultures, treated with solutions of the inventive formulation (Taxol®+compound VI) at the molar ratios paclitaxel:compound VI equal to 1:1, 1:3, 1:6, 1:10, 1:15 and 1:20 in medium with 5% FBS, had the following number of living cells:

1:1: $(27.9\pm2.08)\times10^3$, the cell growth inhibition was 44.6% (p<0.001), and the cell growth inhibition compared to that of Taxol® was increased by 5.4% (p>0.05);

1:3: $(24.2\pm1.66)\times10^3$, the cell growth inhibition was 52.0% (p<0.001), and the cell growth inhibition compared to that of Taxol® was increased by 18.0% (p<0.05);

1:6: $(21.9\pm1.54)\times10^3$, the cell growth inhibition was 56.5% (p<0.001), and the cell growth inhibition compared to that of Taxol® was increased by 25.8% (p<0.01);

1:10: $(21.3\pm1.27)\times10^3$, the cell growth inhibition was 57.7% (p<0.001), and the cell growth inhibition compared to that of Taxol® was increased by 27.8% (p<0.001);

1:15: $(20.9\pm1.40)\times10^3$, the cell growth inhibition was 58.5% (p<0.001), and the cell growth inhibition compared to that of Taxol® was increased by 29.2% (p<0.001);

1:20: $(20.7\pm1.72)\times10^3$, the cell growth inhibition was 58.9% (p<0.001), and the cell growth inhibition compared to that of Taxol® was increased by 29.8% (p<0.002).

Example 37

Preparation and Long Term Storage of the Dried Compound I/Paclitaxel Mixed-micellar System (OF-1)

Paclitaxel (5 mg) in 1 mL methanol and compound 1 (19.5 mg) in 10 ml methanol were mixed in a round-bottom flask. After stirring (2 min) and sonication (1 min) in an Ultrasonic bath, the organic solvent was evaporated on a rotary evaporator under reduced pressure at 40° C. The resulting dry film was dissolved by the addition of water (W) at 25° C. or 0.05 M sodium acetate buffer, pH 5.6 (SAB) to obtain a compound I/paclitaxel micellar solution. The solution, obtained in this process, was filtered through a 0.22 μm sterile filter and lyophilized by a freeze-drying system to obtain the dried compound I/paclitaxel mixed-micellar system (OF-1W) or the dried compound I/paclitaxel mixed-micellar system (OF-1SAB).

The preparations OF-1W and OF-1SAB were stored in powder form for the duration of 1, 36, 64, 92, 127, or 183 days at 4° C.

The OF-1W preparations were reconstituted with: distilled water (OF-1W/W); 10% solution of ethanol (OF-1W/E); 0.15 M solution of NACl (OF-1W/S); 0.05 M sodium acetate buffer, pH 5.6 (OF-1W/SAB); 0.05 M sodium acetate buffer, pH 5.6 in 10% ethanol (OF-1W/SAB/E).

OF-1 SAB was reconstituted with distilled water (OF-1SAB/W).

In all cases a clear solution was obtained immediately. No colour change, precipitation or other noticable changes were observed.

The cytotoxicity of OF-1 was tested on MDA-MB-231 cell line after different periods of storage (results are given in Table 2). The final concentrations of paclitaxel and compound I in the cell culture were $1\cdot10^{-8}$ M and $7\cdot10^{-8}$ M, respectively.

TABLE 2

The Cytotoxicity of OF-1W and OF-1SAB in Human Breast Adenocarcinoma Cell Line MDA-MB-231 after different periods of storage at 4° C.

| Series No. 1 | Drug 2 | Tumor Cell Number, × 10³ 3 | Cell Growth Inhibition, % 4 | p 5 | Positive Effect compared to Taxol ®, % 6 | p 7 |
|---|---|---|---|---|---|---|
| \multicolumn{7}{c}{Storage 1 day} |
| 1 | Negative Control | 57.2 ± 3.26 | — | — | — | — |
| 2 | Taxol ® | 32.1 ± 0.79 | 43.9 | <0.001 | — | — |
| 3 | OF-1W/W | 20.9 ± 2.57 | 63.5 | <0.001 | +34.9 | <0.002 |
| 4 | OF-1W/E | 19.1 ± 2.10 | 66.6 | <0.001 | +40.5 | <0.001 |
| 5 | OF-1W/S | 21.1 ± 2.08 | 63.1 | <0.001 | +34.3 | <0.001 |
| 6 | OF-1W/SAB | 16.7 ± 1.15 | 70.8 | <0.001 | +48.0 | <0.001 |
| 7 | OF-1W/SAB/E | 17.9 ± 1.64 | 68.7 | <0.001 | +44.2 | <0.001 |
| 8 | OF-1SAB/W | 17.6 ± 1.27 | 69.2 | <0.001 | +45.2 | <0.001 |
| \multicolumn{7}{c}{Storage 36 days} |
| 1 | Negative Control | 55.4 ± 1.86 | — | — | — | — |
| 2 | Taxol ® | 29.2 ± 0.62 | 47.3 | <0.001 | — | — |
| 3 | OF-1W/W | 18.7 ± 1.72 | 66.2 | <0.001 | +36.0 | <0.001 |
| 4 | OF-1W/E | 17.9 ± 1.54 | 67.7 | <0.001 | +38.7 | <0.001 |
| 5 | OF-1W/S | 18.3 ± 1.27 | 67.0 | <0.001 | +37.3 | <0.001 |
| 6 | OF-1W/SAB | 14.8 ± 1.89 | 73.3 | <0.001 | +49.3 | <0.001 |
| 7 | OF-1W/SAB/E | 15.2 ± 1.31 | 72.6 | <0.001 | +47.9 | <0.001 |
| 8 | OF-1SAB/W | 15.8 ± 1.18 | 71.5 | <0.001 | +45.9 | <0.001 |
| \multicolumn{7}{c}{Storage 64 days} |
| 1 | Negative Control | 58.7 ± 3.24 | — | — | — | — |
| 2 | Taxol ® | 30.8 ± 1.62 | 47.5 | <0.001 | — | — |
| 3 | OF-1W/W | 19.8 ± 1.49 | 66.3 | <0.001 | +35.7 | <0.001 |
| 4 | OF-1W/E | 19.0 ± 1.56 | 67.6 | <0.001 | +38.3 | <0.001 |
| 5 | OF-1W/S | 19.9 ± 1.37 | 66.1 | <0.001 | +35.4 | <0.001 |
| 6 | OF-1W/SAB | 16.4 ± 1.15 | 72.1 | <0.001 | +46.8 | <0.001 |
| 7 | OF-1W/SAB/E | 17.3 ± 1.43 | 70.5 | <0.001 | +43.8 | <0.001 |
| 8 | OF-1SAB/W | 16.6 ± 0.96 | 71.7 | <0.001 | +46.1 | <0.001 |

TABLE 2-continued

The Cytotoxicity of OF-1W and OF-1SAB in Human Breast Adenocarcinoma Cell Line MDA-MB-231 after different periods of storage at 4° C.

| Series No. | Drug | Tumor Cell Number, × $10^3$ | Cell Growth Inhibition, % | p | Positive Effect compared to Taxol ®, % | p |
|---|---|---|---|---|---|---|
| 1 | 2 | 3 | 4 | 5 | 6 | 7 |
| | | Storage 92 days | | | | |
| 1 | Negative Control | 56.3 ± 2.40 | — | — | — | — |
| 2 | Taxol ® | 31.4 ± 1.86 | 44.2 | <0.001 | — | — |
| 3 | OF-1W/W | 20.1 ± 1.65 | 64.3 | <0.001 | +36.0 | <0.001 |
| 4 | OF-1W/E | 20.0 ± 1.28 | 64.5 | <0.001 | +36.3 | <0.001 |
| 5 | OF-1W/S | 20.2 ± 1.24 | 64.1 | <0.001 | +35.7 | <0.001 |
| 6 | OF-1W/SAB | 16.9 ± 1.02 | 70.0 | <0.001 | +46.2 | <0.001 |
| 7 | OF-1W/SAB/E | 16.5 ± 1.19 | 70.7 | <0.001 | +47.5 | <0.001 |
| 8 | OF-1SAB/W | 15.9 ± 0.83 | 71.8 | <0.001 | +49.4 | <0.001 |
| | | Storage 127 days | | | | |
| 1 | Negative Control | 54.8 ± 1.66 | — | — | — | — |
| 2 | Taxol ® | 31.0 ± 1.48 | 43.4 | <0.001 | — | — |
| 3 | OF-1W/W | 19.7 ± 1.12 | 64.1 | <0.001 | +36.5 | <0.001 |
| 4 | OF-1W/E | 19.5 ± 1.31 | 64.4 | <0.001 | +37.1 | <0.001 |
| 5 | OF-1W/S | 19.6 ± 1.37 | 64.2 | <0.001 | +36.8 | <0.001 |
| 6 | OF-1W/SAB | 16.8 ± 1.15 | 69.3 | <0.001 | +45.8 | <0.001 |
| 7 | OF-1W/SAB/E | 17.5 ± 0.92 | 68.1 | <0.001 | +43.5 | <0.001 |
| 8 | OF-1SAB/W | 16.4 ± 0.76 | 70.1 | <0.001 | +47.1 | <0.001 |
| | | Storage 183 days | | | | |
| 1 | Negative Control | 56.9 ± 1.80 | — | — | — | — |
| 2 | Taxol ® | 31.1 ± 1.36 | 45.3 | <0.001 | — | — |
| 3 | OF-1W/W | 20.0 ± 1.42 | 64.9 | <0.001 | +35.7 | <0.001 |
| 4 | OF-1W/E | 18.3 ± 1.38 | 67.8 | <0.001 | +41.2 | <0.001 |
| 5 | OF-1W/S | 19.9 ± 1.16 | 65.0 | <0.001 | +36.0 | <0.001 |
| 6 | OF-1W/SAB | 16.6 ± 1.09 | 70.8 | <0.001 | +46.6 | <0.001 |
| 7 | OF-1W/SAB/E | 17.2 ± 0.81 | 69.8 | <0.001 | +44.7 | <0.001 |
| 8 | OF-1SAB/W | 15.8 ± 1.25 | 72.2 | <0.001 | +49.2 | <0.001 |

Example 38

Preparation and Long Term Storage of the Dried Compound II/Paclitaxel Mixed-micellar system (OF-2)

The dried compound II/paclitaxel mixed-micellar system (OF-2W) and the dried compound II/paclitaxel mixed-micellar system (OF-2SAB) was obtained as described for the dried compound I/paclitaxel mixed-micellar system (OF-1). The preparations OF-2W and OF-2SAB were stored as a powder for 1 or 180 days at 4° C.

The preparations OF-2W and OF-2SAB were reconstituted either with 0.05 M sodium acetate buffer, pH 5,6 (OF-2W/SAB) or with distilled water (OF-2SAB/W). The cytotoxicity of the solutions OF-2W/SAB and OF-2SAB/W was tested on MDA-MB-231 cell line after storage (the results are given in Table 3). The final concentrations of paclitaxel and compound II in the cell culture were $1·10^{-8}$ M and $7·10^{-8}$ M, respectively.

TABLE 3

Cytotoxicity of OF-2W and OF-2SAB in Human Breast Adenocarcinoma Cell Line MDA-MB-231 after storage at 4° C.

| Series No. | Drug | Tumor Cell Number, × $10^3$ | Cell Growth Inhibition, % | p | Positive Effect compared to Taxol ®, % | P |
|---|---|---|---|---|---|---|
| | | Storage 1 day | | | | |
| 1 | Negative Control | 57.9 ± 2.51 | — | — | — | — |
| 2 | Taxol ® | 31.7 ± 0.94 | 45.3 | <0.001 | — | — |
| 3 | OF-2W/SAB | 17.0 ± 1.02 | 70.6 | <0.001 | +46.4 | <0.001 |
| 4 | OF-2SAB/W | 16.8 ± 0.55 | 71.0 | <0.001 | +47.0 | <0.001 |
| | | Storage 180 days | | | | |
| 1 | Negative Control | 56.6 ± 2.12 | — | — | — | — |
| 2 | Taxol ® | 31.4 ± 1.43 | 44.5 | <0.001 | — | — |
| 3 | OF-2W/SAB | 16.9 ± 1.59 | 70.1 | <0.001 | +46.2 | <0.001 |
| 4 | OF-2SAB/W | 16.5 ± 1.16 | 70.8 | <0.001 | +47.5 | <0.001 |

Example 39

Preparation and Long Term Storage of Dried Compound III/Paclitaxel Mixed-micellar System (OF-3)

The dried compound III/paclitaxel mixed-micellar system (OF-3W) and the dried compoundIII/paclitaxel mixed-micellar system (OF-3SAB) were obtained as described for the dried compound I/paclitaxel mixed-micellar system (OF-1).

The preparations OF-3W and OF-3SAB were stored as a powder for 1 or 180 days at 4° C.

The preparations OF-3W and OF-3SAB were reconstituted either with 0.05 M sodium acetate buffer, pH 5.6 (OF-3W/SAB) or with distilled water (OF-3SAB/W. The cytotoxicity of the solutions OF-3W/SAB and OF-3SAB/W was tested on MDA-MB-231 cell line after storage (the results are given in Table 4). The final concentrations of paclitaxel and compound III in the cell culture were $1 \cdot 10^{-8}$ M and $7 \cdot 10^{-8}$ M, respectively.

TABLE 4

Cytotoxicity of OF-3W and OF-3SAB in Human Breast Adenocarcinoma Cell Line MDA-MB-231 after storage at 4° C.

| Series No. | Drug | Tumor Cell Number, × 10³ | Cell Growth Inhibition, % | p | Positive Effect compared to Taxol ®, % | P |
|---|---|---|---|---|---|---|
| | | Storage 1 day | | | | |
| 1 | Negative Control | 57.9 ± 2.51 | — | — | — | — |
| 2 | Taxol ® | 31.7 ± 0.94 | 45.3 | <0.001 | — | — |
| 3 | OF-3W/SAB | 21.3 ± 2.24 | 63.2 | <0.001 | +32.8 | <0.002 |
| 4 | OF-3SAB/W | 20.9 ± 1.05 | 63.9 | <0.001 | +34.1 | <0.001 |
| | | Storage 180 days | | | | |
| 1 | Negative Control | 56.6 ± 2.12 | — | — | — | — |
| 2 | Taxol ® | 31.4 ± 1.43 | 44.5 | <0.001 | — | — |
| 3 | OF-3W/SAB | 21.0 ± 0.73 | 62.9 | <0.001 | +33.1 | <0.001 |
| 4 | OF-3SAB/W | 20.6 ± 1.37 | 63.6 | <0.001 | +34.4 | <0.001 |

Example 40

Preparation and Long Term Storage of Dried Compound IV/Paclitaxel Mixed-micellar System (OF-4)

The dried compound IV/paclitaxel mixed-micellar system (OF-4W) and the dried compound IV/paclitaxel mixed-micellar system (OF-4SAB) was obtained as described for the dried compound I/paclitaxel mixed-micellar system (OF-1).

The preparations OF-4W and OF-4SAB were stored in powder form for 1 or 180 days at 4° C.

The preparations OF-4W and OF-4SAB were reconstituted with 0.05 M sodium acetate buffer, pH 5.6 (OF-4W/SAB) and with distilled water (OF-4SAB/W), accordingly. The cytotoxicity of solutions OF-4W/SAB and OF-4SAB/W was tested on MDA-MB-231 cell line after storage (results are given in Table 5). The final concentrations of paclitaxel and compound IV in the cell culture were $1 \cdot 10^{-8}$ M and $7 \cdot 10^{-8}$ M, respectively.

TABLE 5

Cytotoxicity of OF-4W and OF-4SAB in Human Breast Adenocarcinoma Cell Line MDA-MB-231 after storage at 4° C.

| Series No. | Drug | Tumor Cell Number, × 10³ | Cell Growth Inhibition, % | p | Positive Effect compared to Taxol ®, % | P |
|---|---|---|---|---|---|---|
| | | Storage 1 day | | | | |
| 1 | Negative Control | 57.9 ± 2.51 | — | — | — | — |
| 2 | Taxol ® | 31.7 ± 0.94 | 45.3 | <0.001 | — | — |

TABLE 5-continued

Cytotoxicity of OF-4W and OF-4SAB in Human Breast Adenocarcinoma Cell Line MDA-MB-231 after storage at 4° C.

| Series No. | Drug | Tumor Cell Number, × 10³ | Cell Growth Inhibition, % | p | Positive Effect compared to Taxol ®, % | P |
|---|---|---|---|---|---|---|
| 3 | OF-4W/SAB | 22.4 ± 0.73 | 61.3 | <0.001 | +29.3 | <0.001 |
| 4 | OF-4SAB/W | 23.0 ± 0.69 | 60.3 | <0.001 | +27.4 | <0.001 |
| | | Storage 180 days | | | | |
| 1 | Negative Control | 56.6 ± 2.12 | — | — | — | — |
| 2 | Taxol ® | 31.4 ± 1.43 | 44.5 | <0.001 | — | — |
| 3 | OF-4W/SAB | 23.1 ± 1.12 | 59.2 | <0.001 | +26.4 | <0.002 |
| 4 | OF-4SAB/W | 22.9 ± 0.85 | 59.5 | <0.001 | +27.1 | <0.001 |

Example 41

Preparation and Long Term Storage of Dried Compound V! Paclitaxel Mixed-micellar System (OF-5)

The dried compound V/paclitaxel mixed-micellar system (OF-5W) or the dried compound V/paclitaxel mixed-micellar system (OF-5SAB) was obtained as described for the dried compound I/paclitaxel mixed-micellar system (OF-1).

The preparations OF-5W and OF-5SAB were stored as a powder for 1, 180 days at 4° C.

OF-5W and OF-5SAB were reconstituted either with 0.05 M sodium acetate buffer, pH 5.6 (OF-5W/SAB) or with distilled water (OF-5SAB/W). The cytotoxicity of solutions OF-5W/SAB and OF-5SAB/W was tested on MDA-MB-231 cell line after storage (the results are given in Table 6). The final concentrations of paclitaxel and compound V in the cell culture were $1 \cdot 10^{-8}$ M and $7 \cdot 10^{-8}$ M, respectively.

TABLE 6

Cytotoxicity of OF-5W and OF-5SAB in Human Breast Adenocarcinoma Cell Line MDA-MB-231 after storage at 4° C.

| Series No. | Drug | Tumor Cell Number, × 10³ | Cell Growth Inhibition, % | p | Positive Effect compared to Taxol ®, % | p |
|---|---|---|---|---|---|---|
| | | Storage 1 day | | | | |
| 1 | Negative Control | 57.9 ± 2.51 | — | — | — | — |
| 2 | Taxol ® | 31.7 ± 0.94 | 45.3 | <0.001 | — | — |
| 3 | OF-5W/SAB | 24.1 ± 1.67 | 58.4 | <0.001 | +24.0 | <0.01 |
| 4 | OF-5SAB/W | 23.3 ± 0.80 | 59.8 | <0.001 | +26.5 | <0.001 |
| | | Storage 180 days | | | | |
| 1 | Negative Control | 56.6 ± 2.12 | — | — | — | — |
| 2 | Taxol ® | 31.4 ± 1.43 | 44.5 | <0.001 | — | — |
| 3 | OF-5W/SAB | 23.9 ± 2.38 | 57.8 | <0.001 | +23.9 | <0.05 |
| 4 | OF-5SAB/W | 23.0 ± 1.32 | 59.4 | <0.001 | +26.8 | <0.002 |

Example 42

Preparation and Long Term Storage of Dried Compound VI/Paclitaxel Mixed-micellar System (OF-6)

The dried compound VI/paclitaxel mixed-micellar system (OF-6W) and the dried compound VI/paclitaxel mixed-micellar system (OF-6SAB) were obtained as described for the dried compound I/paclitaxel mixed-micellar system (OF-1).

The preparations OF-6W and OF-6SAB were stored in powder form for the duration of 1, or 180 days at 4° C.

OF-6W and OF-6SAB were reconstituted with either 0.05 M sodium acetate buffer, pH 5.6 (OF-6W/SAB) or with distilled water (OF-6SAB/W). The cytotoxicity of the solutions OF-6W/SAB and OF-6SAB/W was tested on MDA-MB-231 cell line after storage (the results are given in Table 7). The final concentrations of paclitaxel and compound VI in the cell culture were $1 \cdot 10^{-8}$ M and $7 \cdot 10^{-8}$ M, respectively.

TABLE 7

Cytotoxicity of OF-6W and OF-6SAB in Human Breast Adenocarcinoma Cell Line MDA-MB-231 after storage at 4° C.

| Series No. | Drug | Tumor Cell Number, × 10³ | Cell Growth Inhibition, % | p | Positive Effect compared to Taxol ®, % | P |
|---|---|---|---|---|---|---|
| | | Storage 1 day | | | | |
| 1 | Negative Control | 57.9 ± 2.51 | — | — | — | — |
| 2 | Taxol ® | 31.7 ± 0.94 | 45.3 | <0.001 | — | — |
| 3 | OF-6W/SAB | 24.5 ± 2.39 | 57.7 | <0.001 | +22.7 | <0.02 |
| 4 | OF-6SAB/W | 24.3 ± 1.55 | 58.0 | <0.001 | +23.3 | <0.002 |
| | | Storage 180 days | | | | |
| 1 | Negative Control | 56.6 ± 2.12 | — | — | — | — |
| 2 | Taxol ® | 31.4 ± 1.43 | 44.5 | <0.001 | — | — |
| 3 | OF-6W/SAB | 25.1 ± 1.98 | 55.7 | <0.001 | +20.1 | <0.05 |
| 4 | OF-6SAB/W | 24.0 ± 1.74 | 57.6 | <0.001 | +23.6 | <0.02 |

Although the invention has been described with regard to its preferred embodiments, which constitute the best mode presently known to the inventors, it should be understood that various changes and modifications as would be obvious to one having the ordinary skill in this art may be made without departing from the scope of the invention as set forth in the claims appended hereto.

What is claimed is:

1. A compound having a structural formula chosen among the following (I–VI):

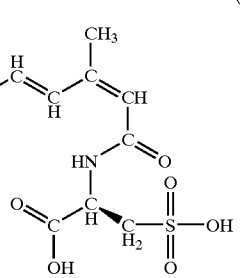

(I)

(N-(ALL-TRANS-RETINOYL)-L-CYSTEIC ACID)

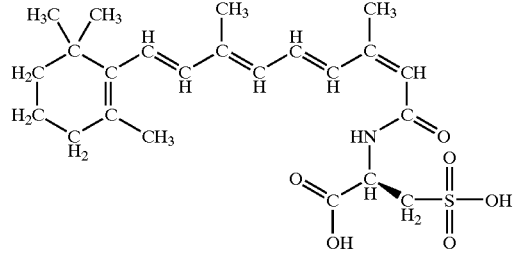

(II)

(N-(13-CIS-RETINOYL)-L-CYSTEIC ACID)

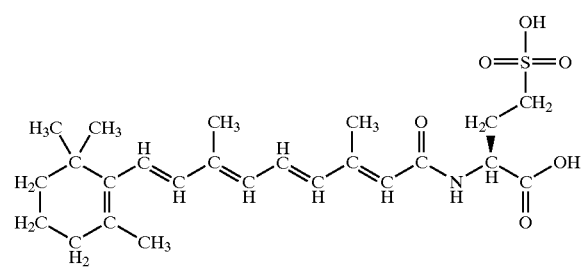

(III)

(N-(ALL-TRANS-RETINOYL)-L-HOMOCYSTEIC ACID)

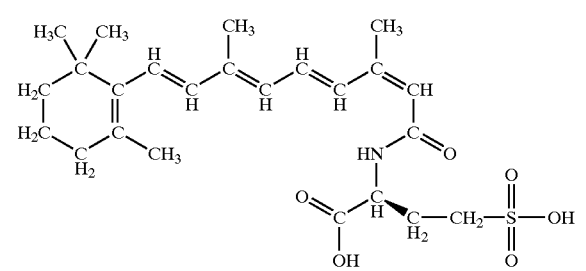

(IV)

(N-(13-CIS-RETINOYL)-L-HOMOCYSTEIC ACID

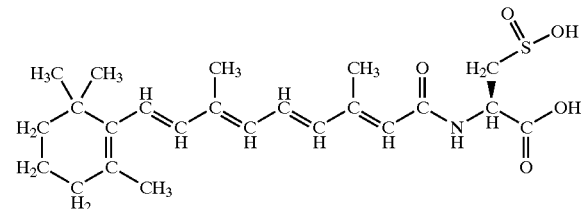

(V)

(N-(ALL-TRANS-RETINOYL)-L-CYSTEINESULFINIC ACID)

-continued

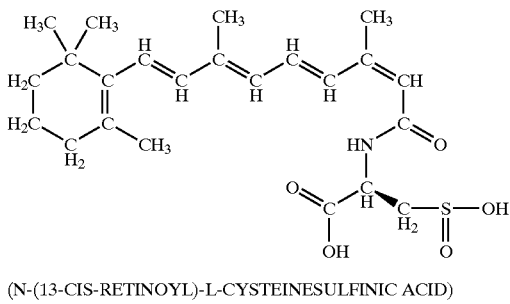

(N-(13-CIS-RETINOYL)-L-CYSTEINESULFINIC ACID) (VI)

2. A pharmaceutically acceptable salt of a compound according to claim 1.

3. A pharmaceutically acceptable sodium salt of a compound according to claim 1.

4. A pharmaceutical composition comprising paclitaxel in a therapeutically effective amount, wherein said composition further comprises a compound according to claim 1 or a derivative thereof.

5. A pharmaceutical composition according to claim 4, wherein said paclitaxel is formulated with polyoxylated castor oil and ethanol.

6. A pharmaceutical composition according to claim 4, wherein the compound of claim 1 is present in the form of its sodium salt.

7. A pharmaceutical composition according to claim 4, wherein the compound of claim 1 is present in acid form.

8. A method for potentiating the efficacy of a therapeutically effective amount of paclitaxel, wherein said paclitaxel is prepared in micellar form with a compound according to claim 1.

9. A method for increasing the solubility of a therapeutically effective amount of paclitaxel, wherein said paclitaxel is prepared in micellar form with a compound according to claim 1.

10. A method for improving the bio-availability of a therapeutically effective amount of paclitaxel, wherein said paclitaxel is prepared in micellar form with a compound according to claim 1.

11. A method for improving the storage properties of a therapeutically effective amount of paclitaxel, wherein said substance is prepared in micellar form with a compound according to claim 1.

12. A method for the treatment of breast, ovarian, and head and neck cancers, wherein a cytotoxic substance is mixed with a compound according to claim 1 and delivered to a patient, wherein the cytotoxic substance is paclitaxel.

13. A method according to claim 12, wherein said paclitaxel is formulated with polyoxylated castor oil and ethanol.

14. A method according to claim 12, wherein the compound of claim 1 is present in the form of its sodium salt.

15. A method according to claim 12, wherein the compound of claim 1 is present in acid form.

16. A method for preparing a water-soluble formulation of paclitaxel, comprising the steps of dissolving paclitaxel in a first solvent, dissolving a compound according to claim 1 in a second solvent, mixing the aliquots of the resulting solutions of paclitaxel and said compound in a desired molar ratio, and evaporating the resulting mixture to dryness.

17. A method for preparing a water-soluble improved formulation of paclitaxel formulated with polyoxylated castor oil and ethanol, comprising the steps of dissolving a compound according to claim 1 in a solvent, evaporation of a desired aliquot of the resulting solution to dryness, and dissolving the residue in said paclitaxel formulated with polyoxylated castor oil and ethanol.

18. A method for preparing a stable storage formulation of paclitaxel, comprising the steps of dissolving paclitaxel in a first solvent, dissolving a compound according to claim 1 in a second solvent, mixing the aliquots of the resulting solutions of paclitaxel and said compound in a desired molar ratio.

19. A method for preparing a formulation of paclitaxel for administration to a patient, comprising the steps of dissolving paclitaxel in a first solvent, dissolving a compound according to claim 1 in a second solvent, mixing the aliquots of the resulting solutions of paclitaxel and said compound in a desired molar ratio, evaporating the resulting mixture to dryness forming a residue of paclitaxel and said compound, dissolving said residue in an aqueous solution, lyophilisation of the solution formed, followed by reconstitution of the lyophilised product using a vehicle suitable for administration to a patient.

20. A method according to claim 16, wherein said first and second solvent are at least one aliphatic alcohol.

21. A method according to claim 18, wherein said first and second solvent are at least one aliphatic alcohol.

22. A method according to claim 19, wherein said first and second solvent are at least one aliphatic alcohol.

23. A method according to claim 16, wherein said first and second solvent is a solvent chosen among ethanol, methanol, 2-propanol and butanol.

24. A method according to claim 18, wherein said first and second solvent is a solvent chosen among ethanol, methanol, 2-propanol and butanol.

25. A method according to claim 19, wherein said first and second solvent is a solvent chosen among ethanol, methanol, 2-propanol and butanol.

26. A method according to claim 16, wherein said first and second solvent is methanol.

27. A method according to claim 17, wherein said first and second solvent is methanol.

28. A method according to claim 18, wherein said first and second solvent is methanol.

29. A method according to claim 19, wherein said first and second solvent is methanol.

30. A method according to claim 16, wherein said paclitaxel is formulated with polyoxylated castor oil and ethanol.

31. A method according to claim 18, wherein said paclitaxel is formulated with polyoxylated castor oil and ethanol.

32. A method according to claim 19, wherein said paclitaxel is formulated with polyoxylated castor oil.

33. A method for the synthesis of sodium salts of compounds according to claim 1 comprising the following consecutive steps:

(a) direct acylation of an amino groups of a precursor in water-organic medium in the presence of $Na_2CO_3$, wherein the precursor is selected from the group consisting of L-cysteic acid, L-homocysteic acid, and L-cysteinesulfinic acid;

(b) separation of insoluble contaminants; and (c) separation of the sodium salts.

34. A method according to claim 33, wherein the water-organic medium is a mixture of tetrahydrofuran-acetonitrile-water.

35. A method according to claim 33, wherein the separation of the insoluble contaminants is performed by the addition of a 2-propanol-water mixture to the water-organic medium.

36. A method according to claim 33, wherein the separation of the sodium salts is performed by the addition of a 2-propanol-methanol mixture to a concentrated solution of the sodium salt of the compound in 2-propanol-water.

* * * * *